United States Patent
Lee et al.

(10) Patent No.: US 11,499,156 B2
(45) Date of Patent: Nov. 15, 2022

(54) BIOMOLECULE IMAGING METHOD USING APTAMER

(71) Applicant: INTEROLIGO CORPORATION, Gyeonggi-do (KR)

(72) Inventors: Jung Hwan Lee, Gyeonggi-do (KR); Jong In Kim, Seoul (KR); Jong Hun Im, Seoul (KR); Jong Ook Lee, Gyeonggi-do (KR); Jin Woo Kim, Daejeon (KR)

(73) Assignee: INTEROLIGO CORPORATION, Gyeonggi-Do (KR)

( * ) Notice: Subject to any disclaimer, the term of this patent is extended or adjusted under 35 U.S.C. 154(b) by 196 days.

(21) Appl. No.: 16/608,645

(22) PCT Filed: Apr. 25, 2018

(86) PCT No.: PCT/KR2018/004770
§ 371 (c)(1),
(2) Date: Oct. 25, 2019

(87) PCT Pub. No.: WO2018/199607
PCT Pub. Date: Nov. 1, 2018

(65) Prior Publication Data
US 2020/0157543 A1   May 21, 2020

(30) Foreign Application Priority Data

Apr. 26, 2017   (KR) .................. 10-2017-0053456
Apr. 23, 2018   (KR) .................. 10-2018-0046550

(51) Int. Cl.
| | | |
|---|---|---|
| C07H 21/04 | (2006.01) |
| C12N 15/115 | (2010.01) |
| A61K 47/60 | (2017.01) |
| A61K 51/04 | (2006.01) |
| G01N 33/533 | (2006.01) |
| G01N 33/534 | (2006.01) |
| G01N 33/574 | (2006.01) |

(52) U.S. Cl.
CPC ............ *C12N 15/115* (2013.01); *A61K 47/60* (2017.08); *A61K 51/0404* (2013.01); *G01N 33/533* (2013.01); *G01N 33/534* (2013.01); *G01N 33/574* (2013.01)

(58) Field of Classification Search
None
See application file for complete search history.

(56) References Cited

U.S. PATENT DOCUMENTS

| 9,309,515 B2* | 4/2016 | Lee | ........................ A61P 35/00 |
| 2009/0004667 A1 | 1/2009 | Zichi et al. | |
| 2015/0005368 A1 | 1/2015 | Lee et al. | |

FOREIGN PATENT DOCUMENTS

| KR | 10-2011-0086433 A | 7/2011 |
| KR | 20130003071 A | 1/2013 |
| KR | 10-2013-0012140 A | 2/2013 |
| KR | 10-1405440 B1 | 6/2014 |
| KR | 10-2015-0045592 A | 4/2015 |

OTHER PUBLICATIONS

Notice of Allowance dated Dec. 1, 2019 from Korean Patent Office in a counterpart Korean Patent Application No. 10-2018-0046550 (all the cited references are listed in this IDS.) (English translation is submitted herewith).
Shawn E. Lupoid et al., "Identification and Characterization of Nuclease-stabilized RNA Molecules That Bind Human Prostate Cancer Cells via the Prostate-specific Membrane Antigen", Cancer Research 62, pp. 4029-4033, 2002.
Dion A. Daniels et al., "A tenascin-C aptamer identified by tumor cell SELEX: Systematic evolution of ligands by exponential enrichment", Proceedings of the National Academy of Sciences of the USA, vol. 100, No. 26, pp. 15416-15421, 2003.
Brian J. Hicke et al., "Tumor Targeting by an Aptamer", The Journal of Nuclear Medicine, vol. 47, No. 4, pp. 668-678, 2006.
Office action dated Dec. 15, 2020 from Japan Intellectual Property Office in a counterpart Japanese Patent Application No. 2019-557747(all the cited references are listed in this IDS.) (English translation is also submitted herewith.).
The extended European Search Report for EP18791814.9 dated Jan. 14, 2021 from European patent office in a counterpart European patent application.
Park Jun Young et al. "Hybridization-based aptamer labeling using complementary oligonucleotide platform for PET and optical imaging", Biomaterials, Elsevier, Amsterdam, NL, vol. 100, May 24, 2016 (May 24, 2016), pp. 143-151, XP029570457 (English translation is submitted herewith.).
International Search Report for PCT/KR2018/004770 dated Aug. 29, 2018.
Kim , Mee Young et al., "In Vitro Selection of RNA Aptamer and Specific Targeting of ErbB2 in Breast Cancer Cells", Nucleic Acid Therapeutics vol. 21, No. 3, pp. 173-178, 2011.

(Continued)

*Primary Examiner* — Kimberly Chong
(74) *Attorney, Agent, or Firm* — The PL Law Group, PLLC

(57) ABSTRACT

A composition for imaging a tumorous disease region includes a fluorescence- or radioactive isotope-labeled ERBB2 aptamer, wherein the ERBB2 aptamer labeled with a radioactive isotope or a fluorescent dye is used to image the tumorous disease region in vivo. The composition may include a labeled hybridized aptamer comprising an aptamer represented as formula 1 hybridized with a labeled-ODN represented as formula 2.

12 Claims, 25 Drawing Sheets

Specification includes a Sequence Listing.

(56) References Cited

OTHER PUBLICATIONS

Moosavian S A et al., "Development of RNA Aptamers as Molecular Probes for HER2+ Breast Cancer Study Using Cell-SELEX", Iranian Journal of Basic Medical Sciences, vol. 18, pp. 576-586, 2015.
Kang, Hye Suk et al., "Isolation of RNA Aptamers Targeting HER-2-overexpressing Breast Cancer Cells Using Cell-SELEX", Bulletin of the Korean Chemical Society, vol. 30, No. 8, pp. 1827-1831, 2009.
Guizhi Zhu et al., "Combinatorial Screening of DNA Aptamers for Molecular Imaging of HERZ in Cancer", Bioconjugate Chemistry, 28, pp. 1068-1075, 2017.
Orit Jacobson et al., "PET imaging of Tenascin-C with a Radiolabeled single-strand DNA aptamer", Journal of nuclear medicine: official publication, Society of Nuclear Medicine, 56: 616-21, 2015.

\* cited by examiner

Lane 1 : 1kb DNA Marker
Lane 2 : Annealing at 95°C for 5min mix Cholesteryl-{AP001-24}-ODN & cODN-Cy5
Lane 3 : Annealing at 95°C for 5min mix Cholesteryl-{AP001-24}-ODN-idT & cODN-Cy5
Lane 4 : cODN-Cy5
Lane 5 : Annealing at 95°C for 5min mix PEGylated-{AP001-25}-ODN & cODN-Cy5
Lane 6 : Annealing at 95°C for 5min mix PEGylated-{AP001-25}-ODN-idT & cODN-Cy5

FIG. 5
Confocal image for KPL4 cell line
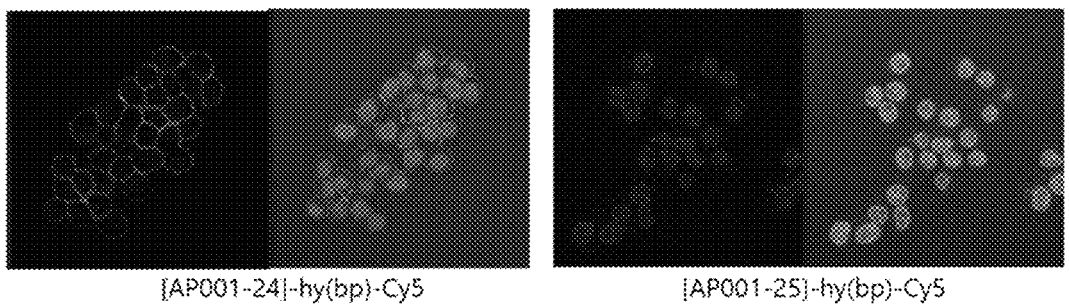
[AP001-24]-hy(bp)-Cy5  [AP001-25]-hy(bp)-Cy5
Confocal image for N87 cell line
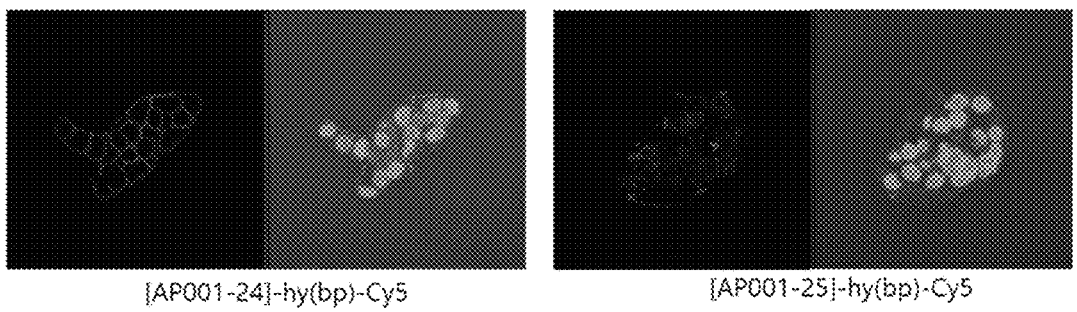
[AP001-24]-hy(bp)-Cy5  [AP001-25]-hy(bp)-Cy5
Confocal image for SK-BR-3 cell line
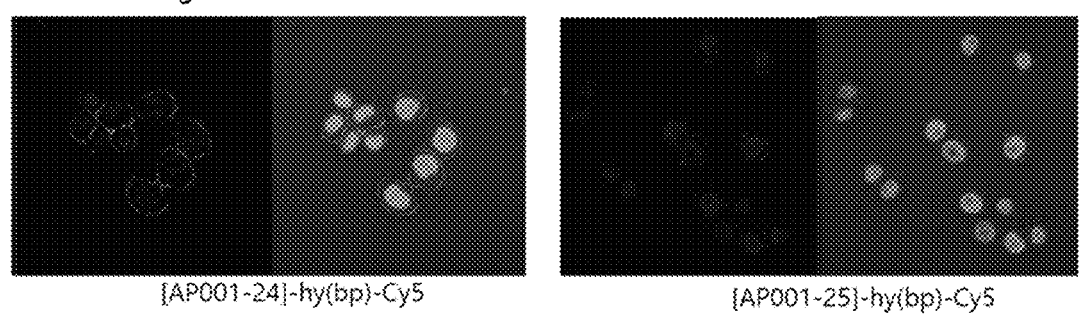
[AP001-24]-hy(bp)-Cy5  [AP001-25]-hy(bp)-Cy5

FIG. 6A
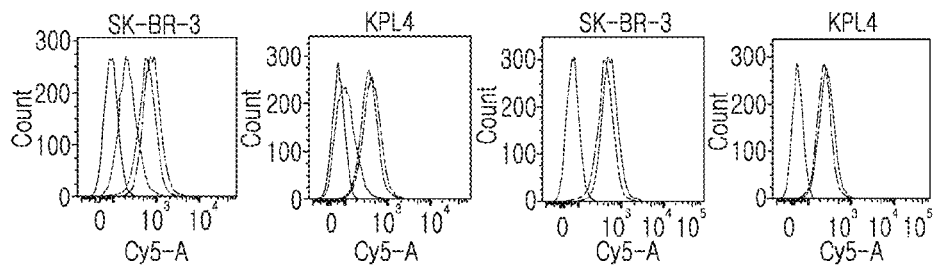
Green : no treat, Orange : [AP001-24]-ODN
Blue : [AP001-24]-ODN-idT, Red : cODN-Cy5
Orange : no treat, Blue : [AP001-24]-ODN
Red : [AP001-24]-ODN-idT
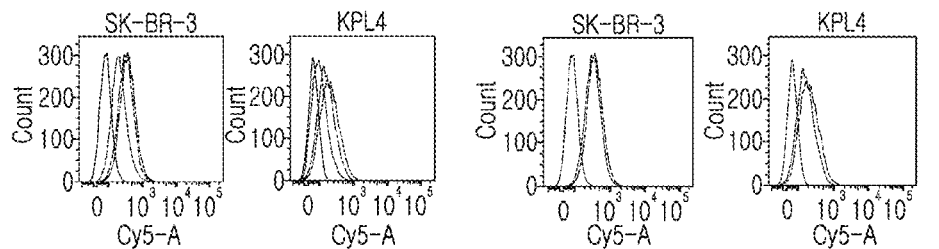
Green : no treat, Orange : [AP001-24]-ODN
Blue : [AP001-24]-ODN-idT, Red : cODN-Cy5
Orange : no treat, Blue : [AP001-24]-ODN
Red : [AP001-24]-ODN-idT
FIG. 6B
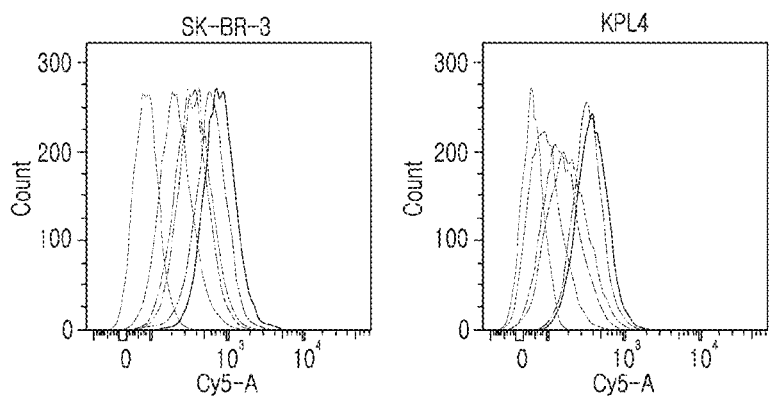
Plink : No treat, Green : [AP001-24]-ODN, Khaki : [AP001-24]-ODN-idT
Orange : [AP001-25]-ODN, Blue : [AP001-25]-ODN-idT Red : cODN-Cy5

| [AP001-24]-hy(bp)-L-F¹⁸ | KPL4 | Liver | R. Kidney | L.Kidney |
|---|---|---|---|---|
| KPL4 M#2 post 30 min | 0.721 ± 0.137 | 2.880 ± 0.428 | 6.511 ± 1.018 | 6.863 ± 0.600 |
| KPL4 M#2 post 60 min | 0.445 ± 0.056 | 1.111 ± 0.107 | 2.065 ± 0.515 | 2.405 ± 0.549 |
| KPL4 M#2 post 120 min | 0.154 ± 0.035 | 0.287 ± 0.077 | 0.712 ± 0.172 | 0.639 ± 0.121 |

| [AP001-24]-idT-hy(bp)-L-F[18] | KPL4 | Liver | R. Kidney | L.Kidney |
|---|---|---|---|---|
| KPL4 M#1 post 30 min | 1.416 ± 0.337 | 5.107 ± 0.479 | 8.811 ± 2.377 | 9.726 ± 3.253 |
| KPL4 M#2 post 30 min | 1.527 ± 0.268 | 4.515 ± 0.428 | 8.341 ± 1.694 | 8.630 ± 2.937 |
| KPL4 M#3 post 30 min | - | - | - | - |
| KPL4 M#3 post 30 min | 1.52 ± 0.323 | 4.054 ± 0.409 | 7.797 ± 0.932 | 9.986 ± 2.327 |
| KPL4 M#1 post 60 min | 1.277 ± 0.161 | 1.807 ± 0.138 | 2.854 ± 0.429 | 2.809 ± 0.409 |
| KPL4 M#2 post 60 min | 1.112 ± 0.105 | 1.631 ± 0.271 | 2.975 ± 0.707 | 2.939 ± 0.880 |
| KPL4 M#3 post 60 min | 1.049 ± 0.165 | 1.402 ± 0.163 | 3.048 ± 1.348 | 2.778 ± 1.367 |
| KPL4 M#4 post 60 min | 0.786 ± 0.196 | 2.585 ± 0.544 | 3.434 ± 0.941 | 3.096 ± 0.323 |
| KPL4 M#1 post 120 min | 0.641 ± 0.138 | 0.514 ± 0.098 | 0.825 ± 0.213 | 0.862 ± 0.259 |

| Cholesteryl-(AP001-24)-hy(bp)-L-F18 | KPL4 | Liver | R. Kidney | L.Kidney |
|---|---|---|---|---|
| KPL4 M#1 post 30 min | 0.898 ± 0.119 | 2.91 ± 0.329 | 7.594 ± 1.369 | 7.493 ± 1.053 |
| KPL4 M#2 post 30 min | 0.706 ± 0.267 | 2.194 ± 0.223 | 5.635 ± 0.986 | 5.760 ± 1.200 |
| KPL4 M#1 post 60 min | 0.667 ± 0.144 | 0.984 ± 0.195 | 2.679 ± 0.566 | 2.720 ± 0.703 |
| KPL4 M#2 post 60 min | 0.428 ± 0.181 | 0.747 ± 0.116 | 1.533 ± 0.447 | 1.404 ± 0.262 |
| KPL4 M#2 post 120 min | 0.255 ± 0.144 | 0.261 ± 0.109 | 0.669 ± 0.225 | 0.513 ± 0.182 |

| Cholesteryl-[AP001-24]-idT-hy(bp)-L-F18 | KPL4 | Liver | R. Kidney | L.Kidney |
|---|---|---|---|---|
| KPL4 M#3 post 30 min | - | - | - | - |
| KPL4 M#4 post 30 min | 1.145 ± 0.272 | 2.853 ± 0.786 | 7.696 ± 1.319 | 7.454 ± 1.053 |
| KPL4 M#3 post 60 min | - | - | - | - |
| KPL4 M#4 post 60 min | 0.627 ± 0.150 | 2.207 ± 0.599 | 2.059 ± 0.652 | 1.071 ± 0.240 |
| KPL4 M#4 post 120 min | 0.294 ± 0.116 | 0.271 ± 0.083 | 0.669 ± 0.194 | 0.695 ± 0.278 |

| PEGylated-[AP001-24]-hy(bp)-L-F[18] | KPL4 (%ID/g) |
|---|---|
| KPL4 M#4 post 30 min | 1.005 ± 0.212 |
| KPL4 M#4 post 60 min | 0.727 ± 0.210 |

FIG. 20
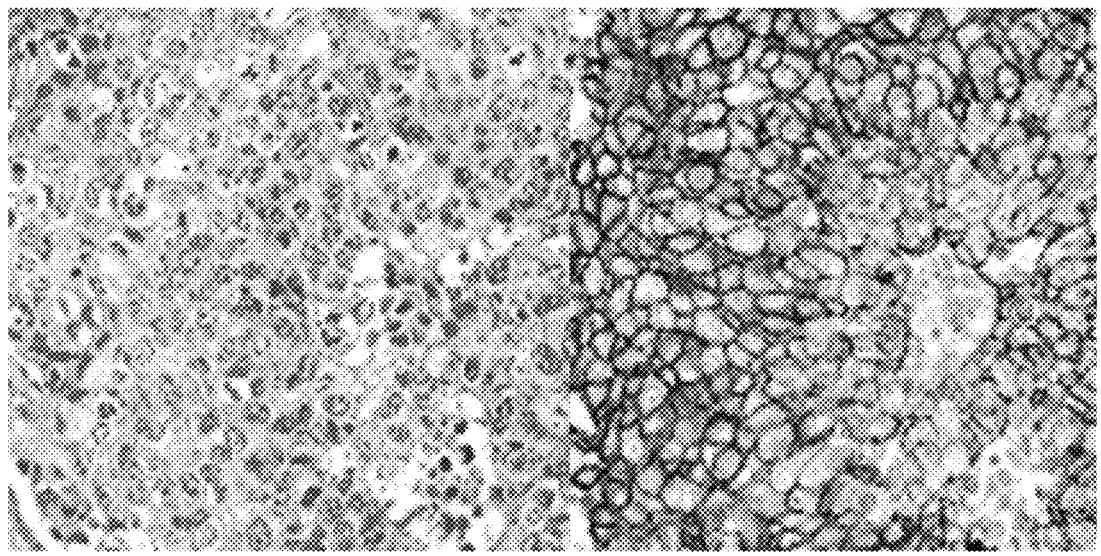
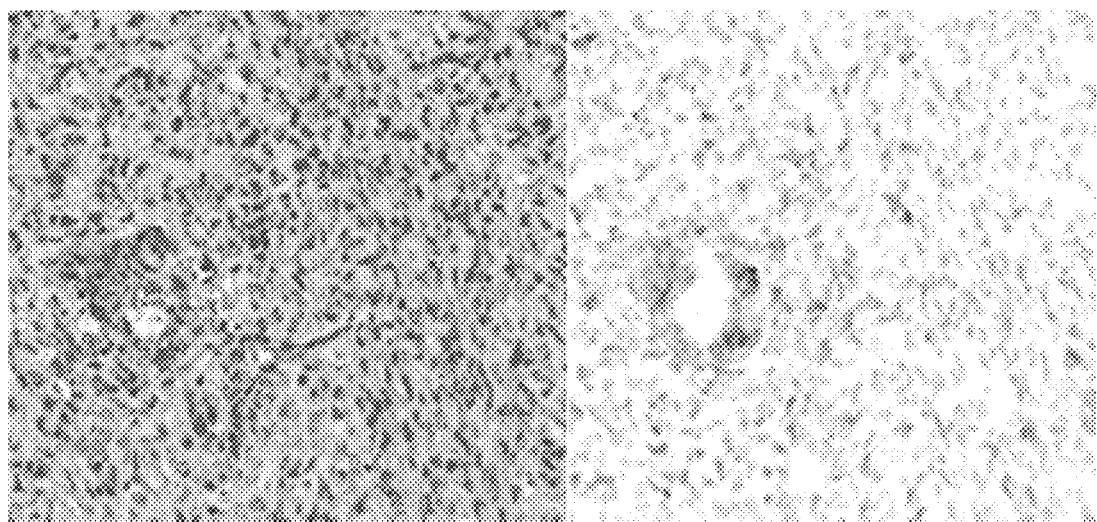

BIOMOLECULE IMAGING METHOD USING APTAMER

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/004770, filed on Apr. 25, 2018, which claims priority to the benefit of Korean Patent Application No. 10-2017-0053456 filed on Apr. 26, 2017 and 10-2018-0046550 filed on Apr. 23, 2018 in the Korean Intellectual Property Office, the entire contents of which are incorporated herein by reference.

TECHNICAL FIELD

The present invention relates to a biomolecule imaging method using aptamer, and more particularly, to a method for obtaining images by using aptamer labeled with isotope and binding the same to a human epidermal growth factor receptor 2 (HER2) expressing cell line.

BACKGROUND ART

The etymology of aptamer was derived from the Latin meaning of "aptus (exactly right)" and the Greek meaning "meros (partial)." The aptamer is a single-stranded nucleic acid having a DNA sequence consisting of about 20 to 90 bases. Usually, aptamer highly specific to a target molecule and having a high affinity thereto is screened through an artificial evolution method such as in vitro SELEX (Systematic Evolution of Ligands by Exponential Enrichment) as an aptamer excavation technology. Therefore, the aptamer is regarded as a very suitable reagent to determine or find a degree of expression of specific molecules to be targeted by the aptamer. In several aspects such as reduced production costs, easy synthesis, low toxicity, no occurrence of immune response, and no production of the aptamer in an animal system unlike an antibody, etc., the aptamer has advantages as compared to the antibody. The aptamer is a reagent relatively newly developed in diagnosis fields. A number of aptamers for a wide variety of targets including thrombin, nucleolin, PSMA, TNC and virus origin proteins have been developed. In therapeutic fields, VEFG target aptamer was developed and approved as elderly macular degeneration therapeutic agents by the FDA in 2004. Recently, so many types of aptamers are under development in pre-clinical and clinical phases and a number of experiments relevant to diagnosis and treatment are in the process.

HER2 is a cancer gene very well known in the art, which is increased or over-expressed in about 15 to 30% of breast cancer. Further, this is a factor associated with high recurrence and poor prognosis of different cancers. There are two signaling systems activated by HER2, including a MAPK route promoting cell proliferation and a PI3K-AKT route increasing survival of cancer cells. Therefore, the above factor is a highly preferred target for application in treatment of cancer. In this regard, transtuzumab and pertuzummab for targeting HER2 currently exist as therapeutic monoclonal antibodies well known and available in the art, and have been found to be effective in clinical applications. Before then, several HER2 targeting DNA/RNA aptamers were disclosed through traditional SELEX methods and cell-based SELEX. Moreover, examples of pharmaceutically utilizing cancer inhibitory properties of the HER2 aptamers have been recently reported.

Meanwhile, molecule images may be a non-invasive method that enables real-time visualization of biochemical events in a cellular molecular level in regard to living cells or tissues or objects without damage. The aptamer modified into a magnetic nano-material or fluorescent material may be provided as a preferred substance for targeted fluorescence imaging or magnetic resonance imaging (MRI). Some in vivo MRI studies demonstrated efficiently targeted cancer in mice having cancer. However, due to metabolic changes occurring before anatomic changes, PET is distinctly more advantageous in a diagnostic aspect than anatomical techniques such as computed tomography (CT) and MRI. In clinical applications, PET is broadly used in basic research and preclinical fields. For instance, the PET may be used to verify or validate analysis of new radio-therapeutics, therapeutic efficacy of novel therapeutic agents and in vivo distribution of drugs. Merits of PET may include probe depth, superior sensitivity, quantitative data and convertible-ness (i.e., phase progress) from pre-clinical trials to clinical trials. That is, the PET is a representative molecule imaging device that can detect biochemical changes in a target level of living biomolecules and is highly sensitive, thereby being used in a wide range of applications including basic science and pre-clinical area. Cancer targeting using aptamer is a biomolecule imaging technique proposed in recent years, and for example, many researchers including Hicke et. al. have adopted aptamer in molecule imaging. They have bound $^{99m}TC$ to an aptamer called TTA1 bound to tenascin-C as an extracellular protein through a covalent bond, and then imaged cancer using a gamma-camera in vivo. Since then, PET imaging has also been implemented by other researcher teams.

However, implementation of PET imaging using HER2-specific ERBB2 aptamer has not been disclosed.

SUMMARY

Aptamer is one of nucleic acids and a material with high specificity and affinity to a target molecule. It is an object of the present invention to provide molecular images in vivo using radioactive isotope or fluorescent dye-labeled aptamer.

FIG. 1 is a mechanism schematic view illustrating radioactive isotope or fluorescence-labeled ERBB2 aptamer.

According to the present invention, HER2 aptamer labeled with a radioactive isotope or fluorescent dye is used for in vivo imaging.

In flow cytometric analysis, ERBB2 aptamer is almost not bound to MDA-MB231 cell line without expression of HER2, but may have very high affinity to BT474 as a HER2 expressing cell line. Similarly, it is observed from images obtained by a confocal microscope that the aptamer is bound to HER2 expressed breast cancer cell line, while showing only minimum binding to HER2 non-expressing cells. Molecular images of positron emission tomography for a mouse transplanted in vivo with BT474 cancer cell line have demonstrated a significant increase in intake of $^{18}F$-labeled HER2-specific ERBB2 aptamer. ERBB2 aptamer may be preferentially bound to HER2 expressed breast cancer cell line both in vitro and in vivo, and the reason is that HER2 structure is possibly recognized on the surface of the cells.

ERBB2 aptamer labeled with a radioactive isotope such as $^{18}F$ or a fluorescent dye may recognize HER2 expression in human breast cancer cells and enable adequate visualization. These results suggest a target treatment application using such an isotope or fluorescent dye-labeled ERBB2 aptamer to HER2-positive breast cancer cells or a potential application method how to treat the same.

BRIEF DESCRIPTION OF THE DRAWINGS

FIG. 5 illustrates confocal image results of KPL4, N87 and SK-BR cell lines treated with R-[ERBB2 aptamer]-X-hy(bp)-Cy5, including confocal microscopic images of [AP001-24]-hy(bp)-Cy5 and [AP001-25]-hy(bp)-Cy5 aptamer in HER2-positive cell line, in particular: (a) treatment of KPL4, HER2-positive breast cancer cell line with Cy-labeled aptamer; (b) treatment using the same aptamer in N87 cancer cell line; and (c) treatment using the same aptamer in SK-BR-3 cancer cell line (marker DAPI: blue, and Cy5-aptamer: red).

FIGS. 6A and 6B illustrate results of FACS analysis of KPL4, N87 and SK-BR cell lines treated with R-[ERBB2 aptamer]-X-hy(bp)-Cy5, respectively.

In this regard, Table 3 shows a hybridization structure of R-[ERBB2 aptamer]-ODN-X (R=H, cholesterol or PEG, and X=H or idT) and cODN-L-$F^{18}$ (L=linker), which is represented by R-[ERBB2 aptamer]-X-hy(bp)-L-$F^{18}$.

Figure 7A:
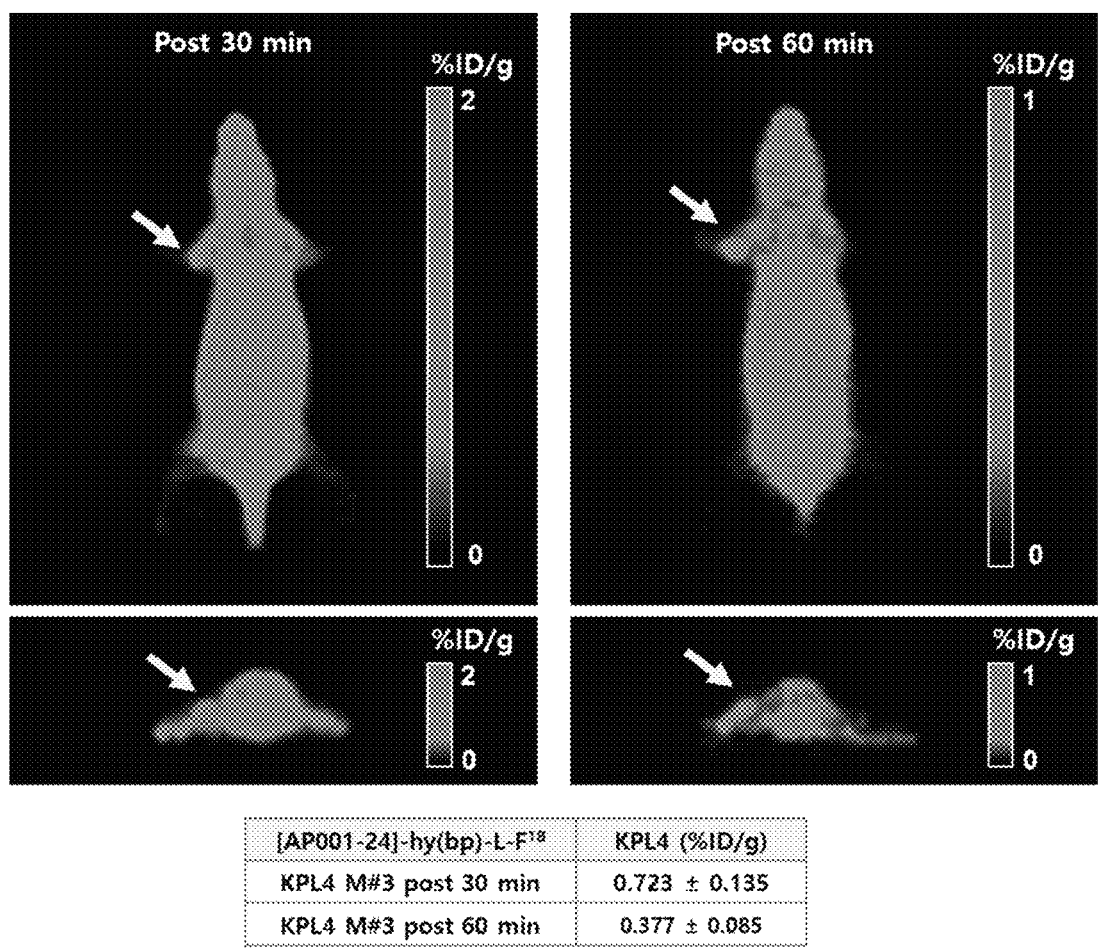
Figure 7B:
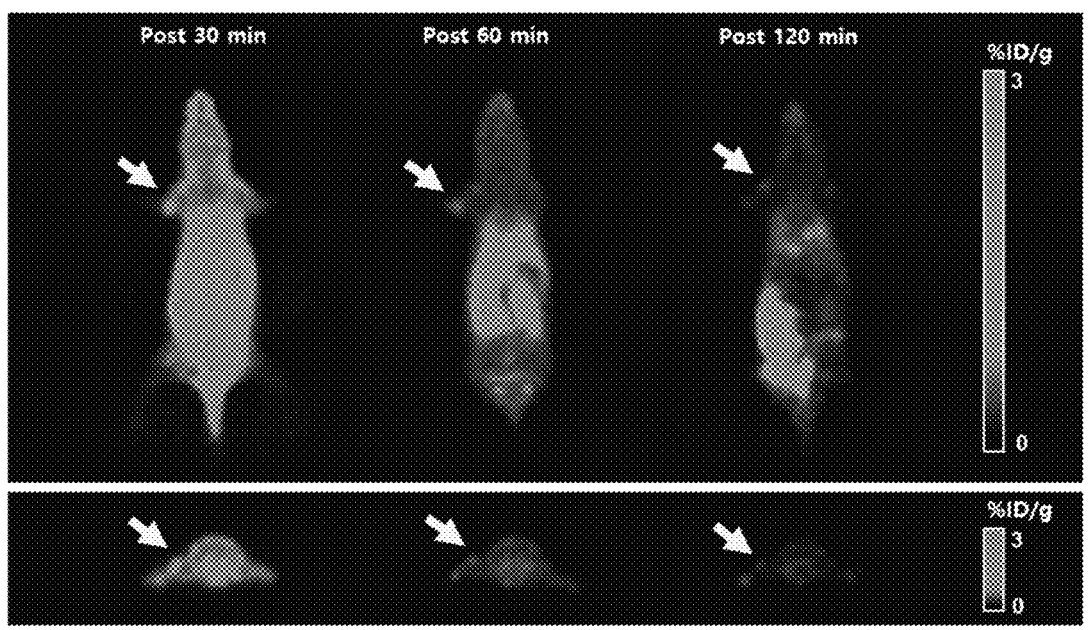

FIGS. 7A and 7B illustrate results of microPET images of [AP001-24]-hy(bp)-L-$F^{18}$.

Figure 8A:
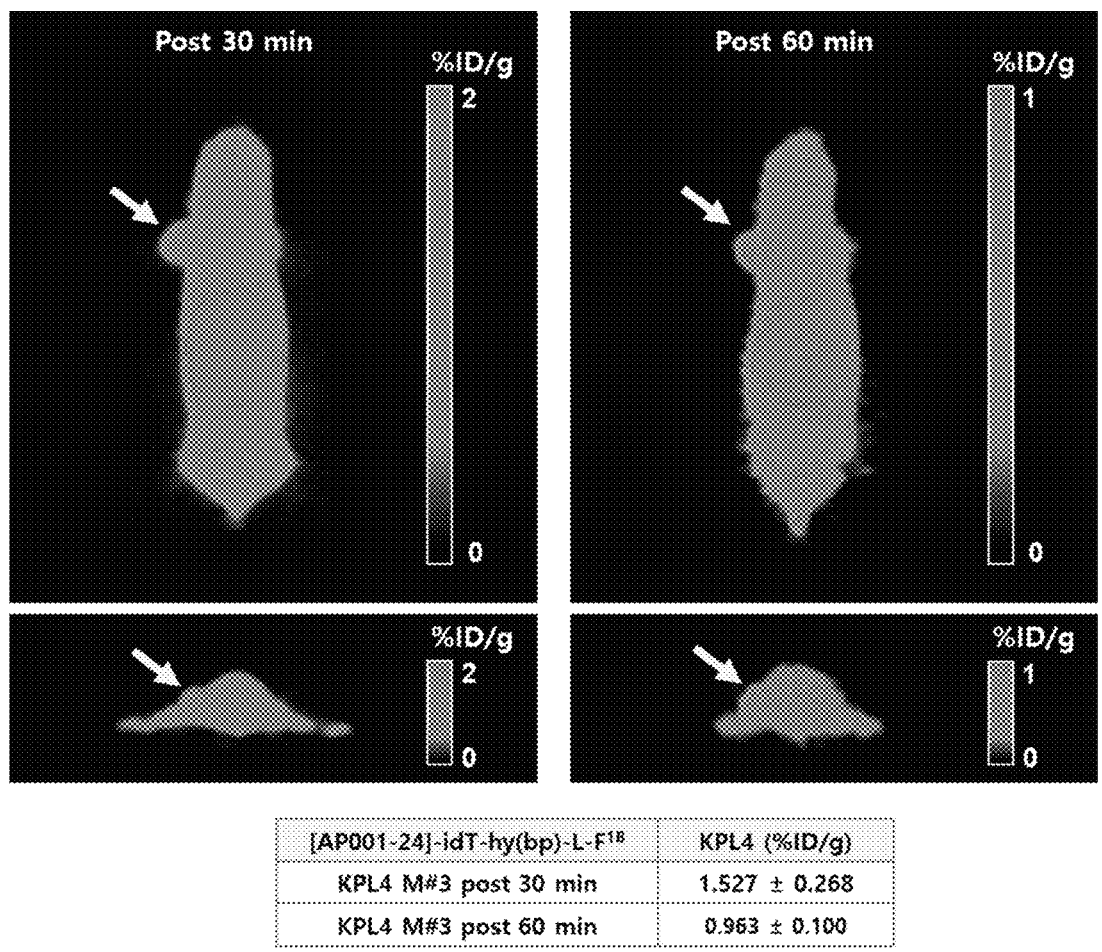
Figure 8B:
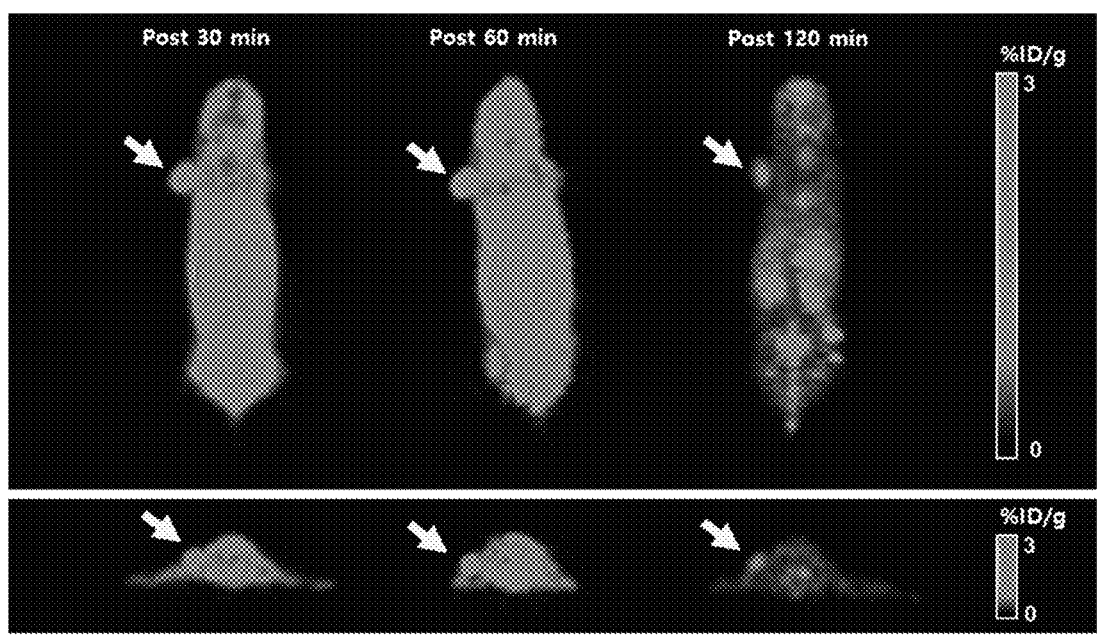

FIGS. 8A and 8B illustrate results of microPET images of [AP001-24]-idT-hy(bp)-L-$F^{18}$.

Figure 9A:
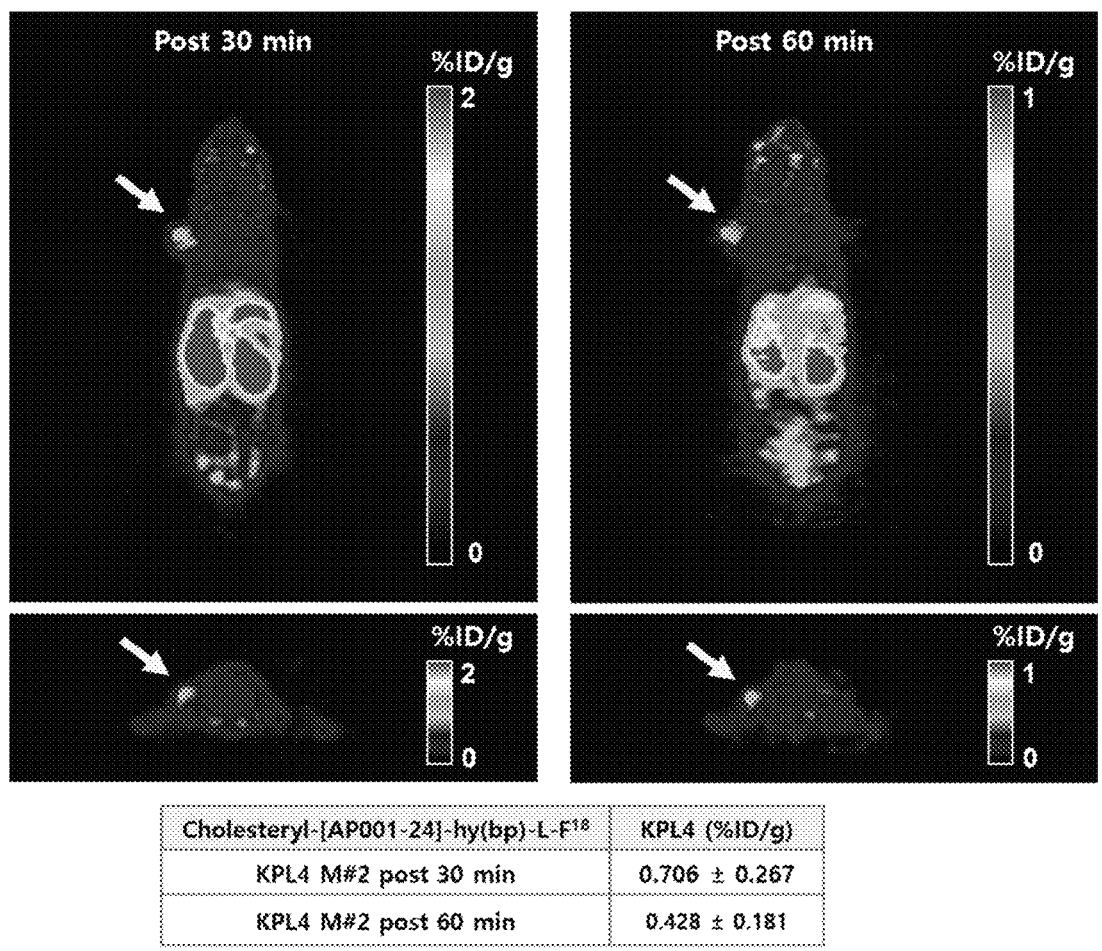
Figure 9B:
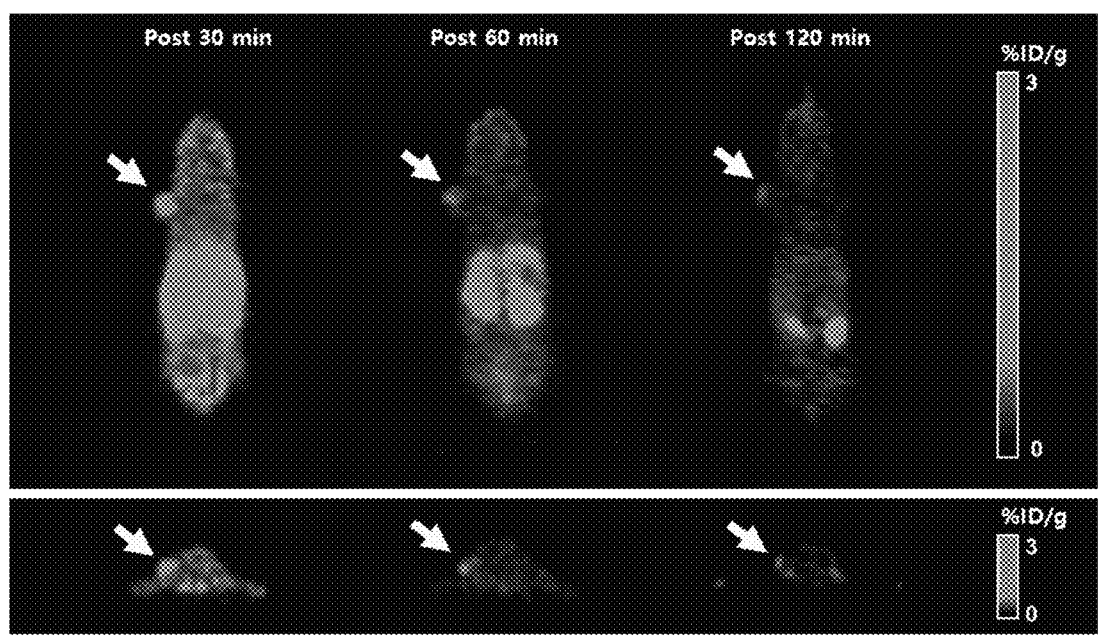

FIGS. 9A and 9B illustrate results of microPET images of cholesteryl-[AP001-24]-hy(bp)-L-$F^{18}$.

Figure 10A:
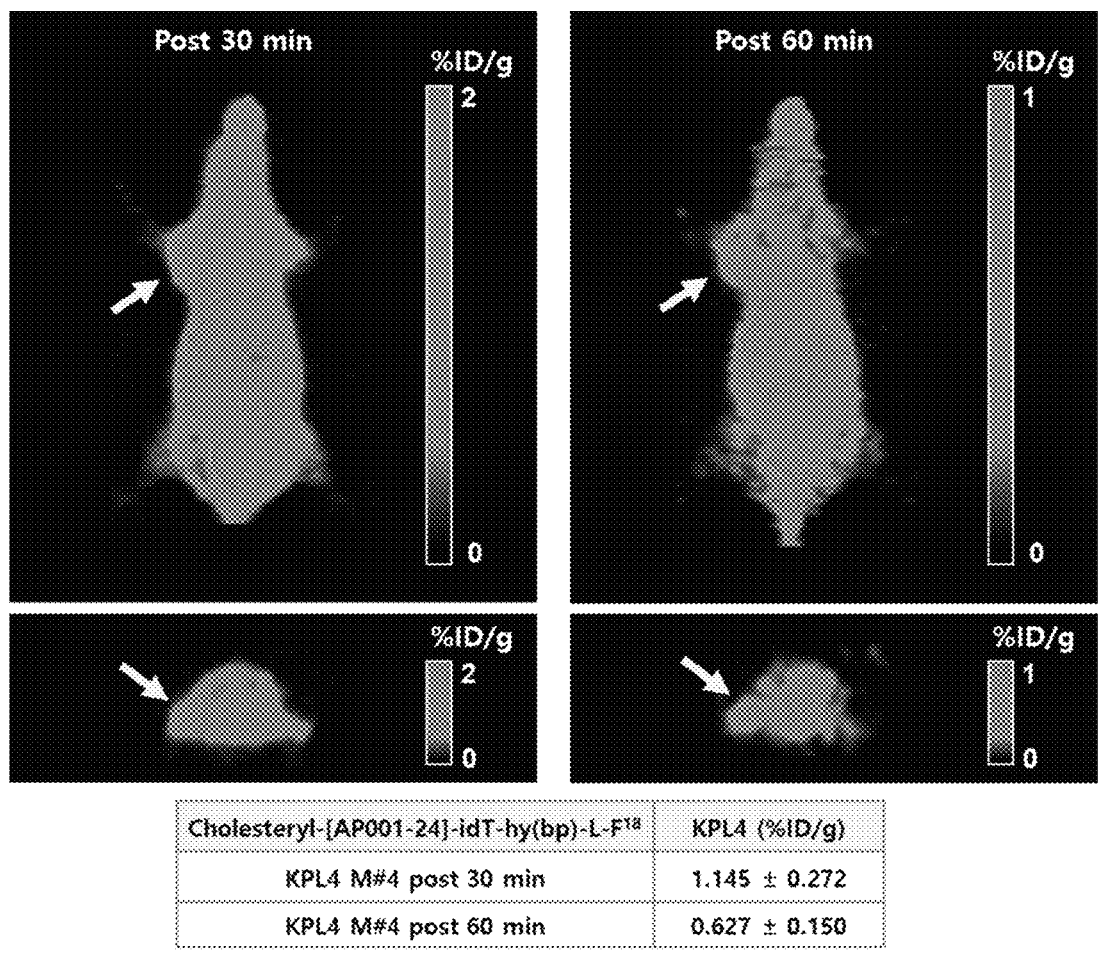
Figure 10B:
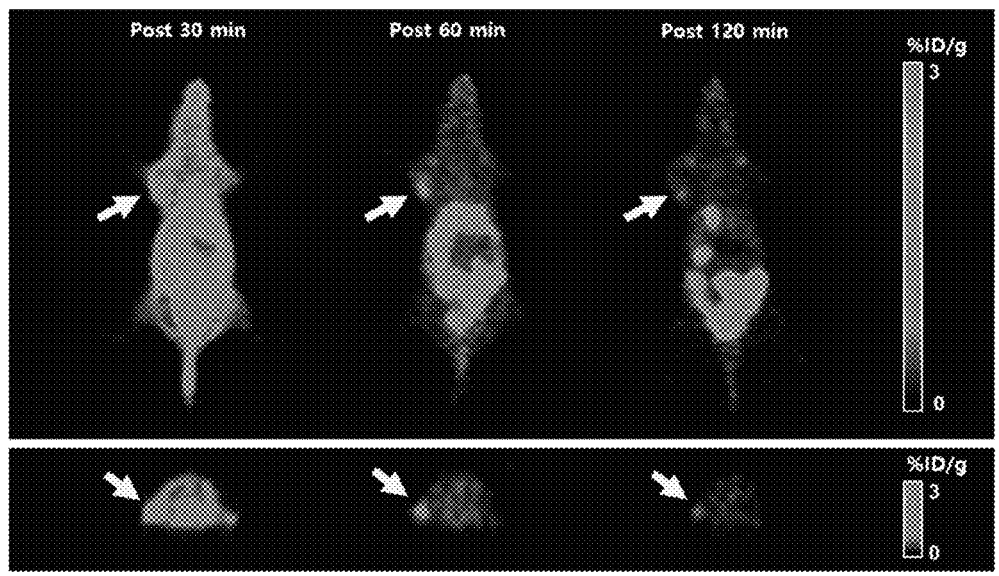

FIGS. 10A and 10B illustrate results of microPET images of cholesteryl-[AP001-24]-idT-hy(bp)-L-$F^{18}$.

Figure 11:
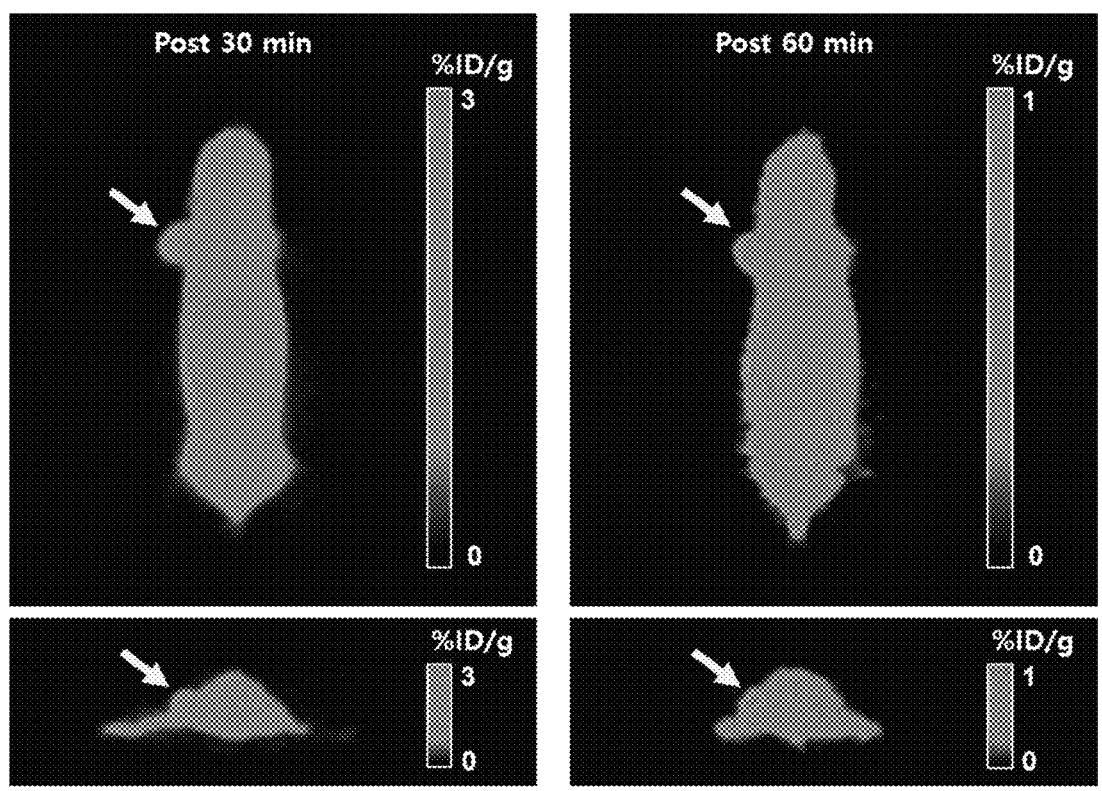

FIG. 11 illustrates results of microPET images of PEGylated-[AP001-24]-hy(bp)-L-$F^{18}$.

Figure 12:
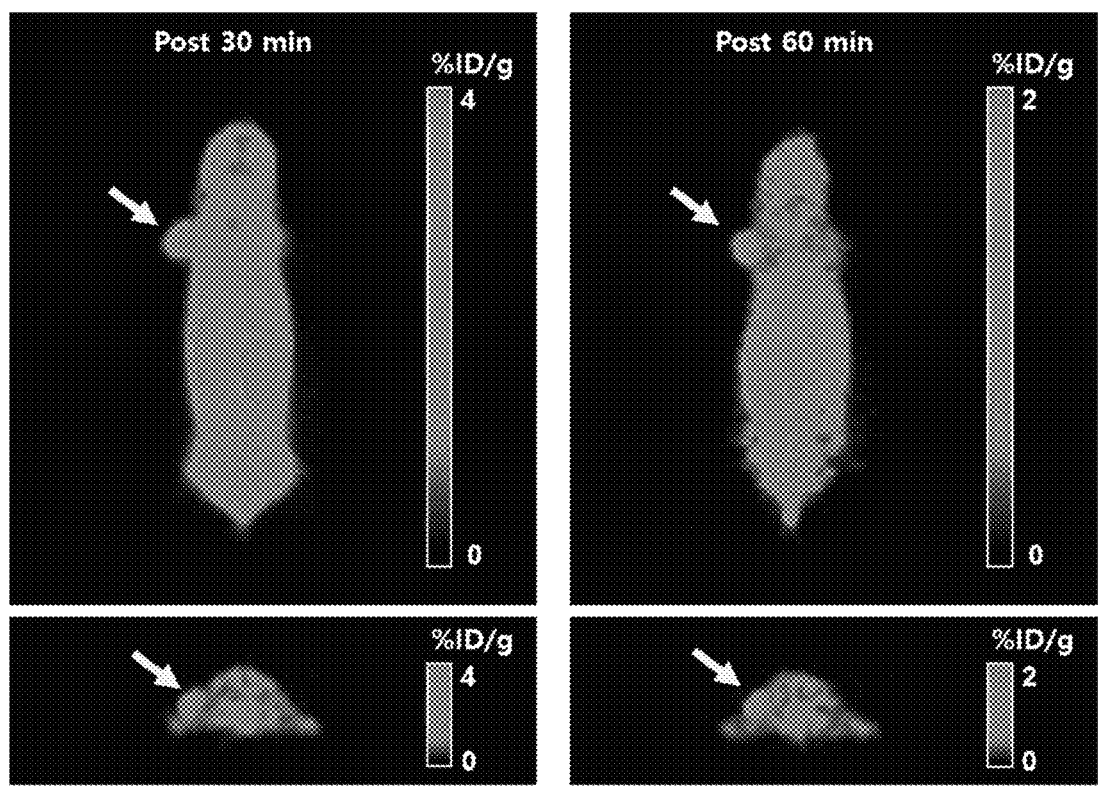

FIG. 12 illustrates results of microPET images of PEGylated-[AP001-24]-idT-hy(bp)-L-$F^{18}$.

Figure 13:
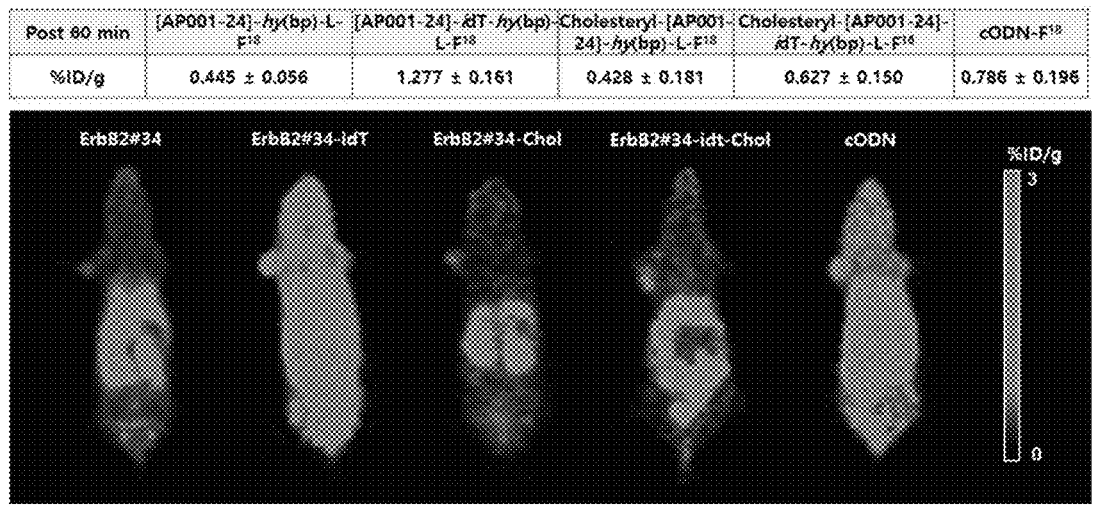

FIG. 13 is comparative images of [AP001-24]-hy(bp)-L-$F^{18}$, [AP001-24]-idT-hy(bp)-L-$F^{18}$, cholesteryl-[AP001-24]-hy(bp)-L-$F^{18}$ and cholesteryl-[AP001-24]-idT-hy(bp)-L-$F^{18}$ in mice having KPL4 cancer.

Figure 14:
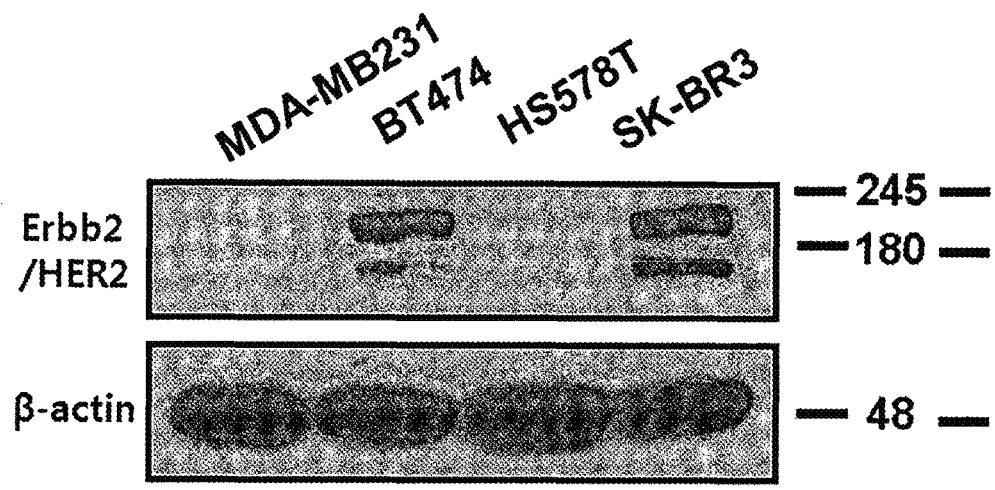

FIG. 14 illustrates determination of a degree of HER2 expression in human breast cancer cell line by Western blot.

Figure 15A:
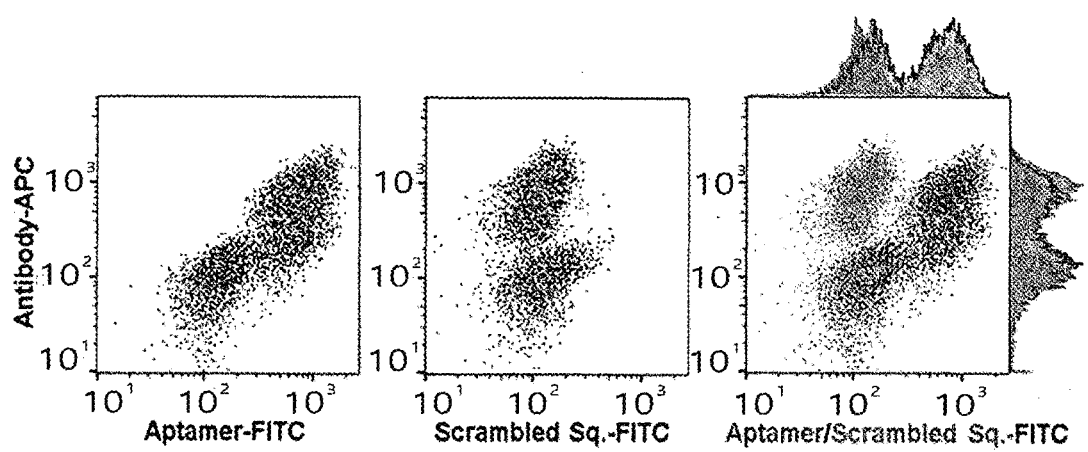
Figure 15B:
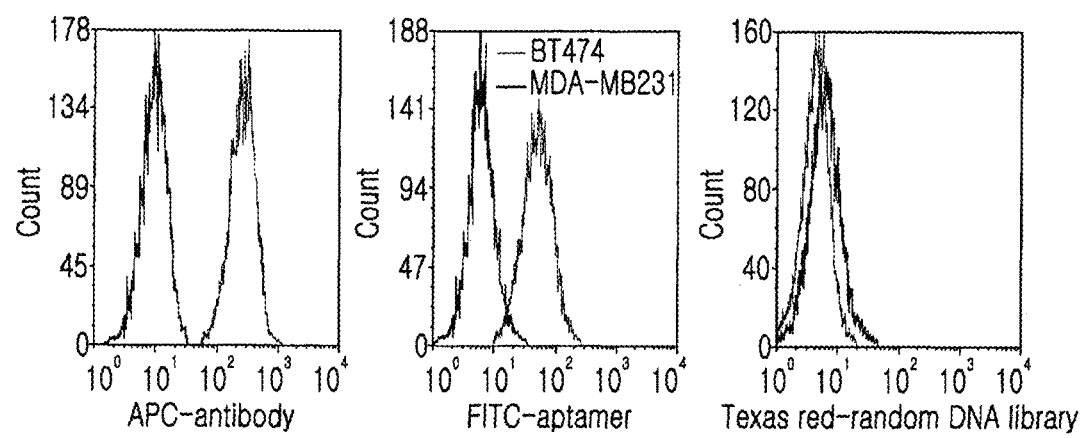

FIGS. 15A and 15B illustrate flow cytometric analysis of breast cancer cell line using HER2 antibody and ERBB2 aptamer (AP001-25), wherein: (a) a viscosity table shows fluorescent signals from antibodies to BT474 (HER2-positive cell line) and MDA-MB231 (HER2-negative cell line), with ERBB2 aptamer (AP001-25) (red) or DNA sequence of a control group (blue); and (b) flow cytometric analysis graphs of both cell lines using the antibody, ERBB2 aptamer (AP001-25) and a negative control are included.

Figure 16A:
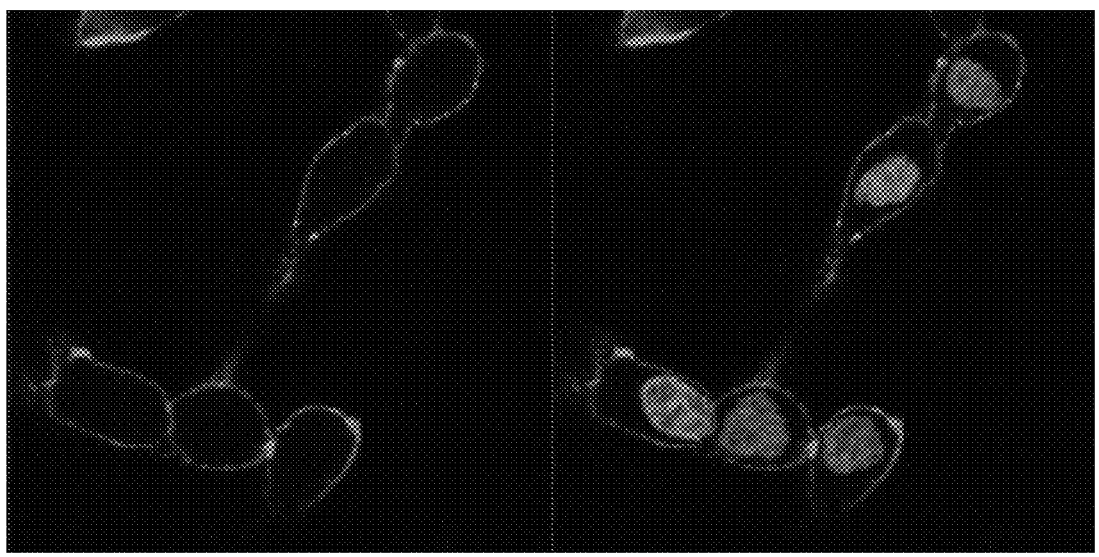
Figure 16B:
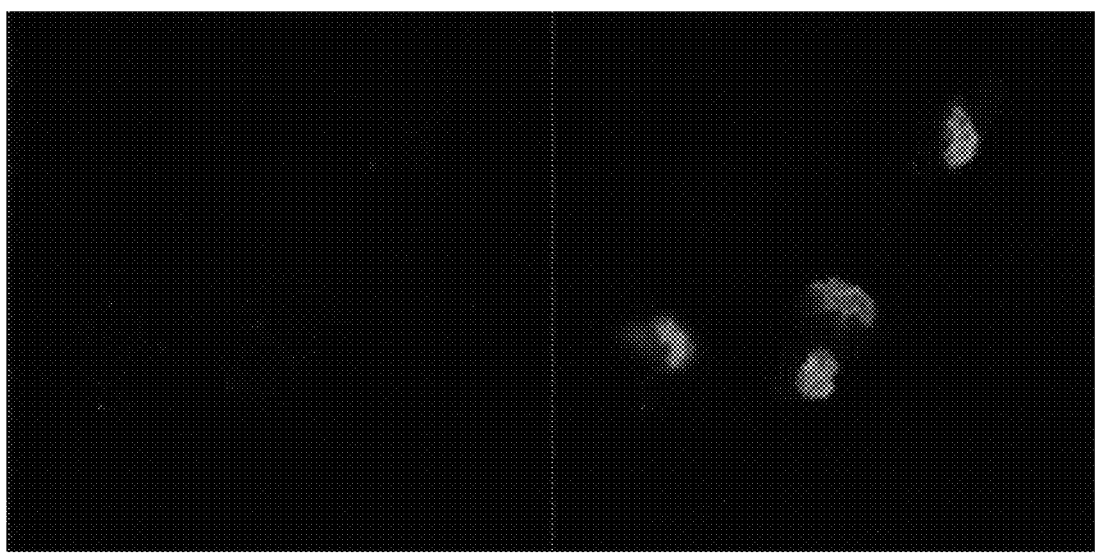

FIGS. 16A and 16B illustrate confocal microscopic images of the selected ERBB2 aptamer (AP001-25) in HER2-positive cell line, in particular: (a) treatment of BT474, HER2 positive breast cancer cell line with FITC marker aptamer; and (b) treatment using the same ERBB2 aptamer (AP001-25) in MDA-MB231 cancer cell line (marker DAPL: blue, and FITC-ERBB2 aptamer: green).

Figure 17:
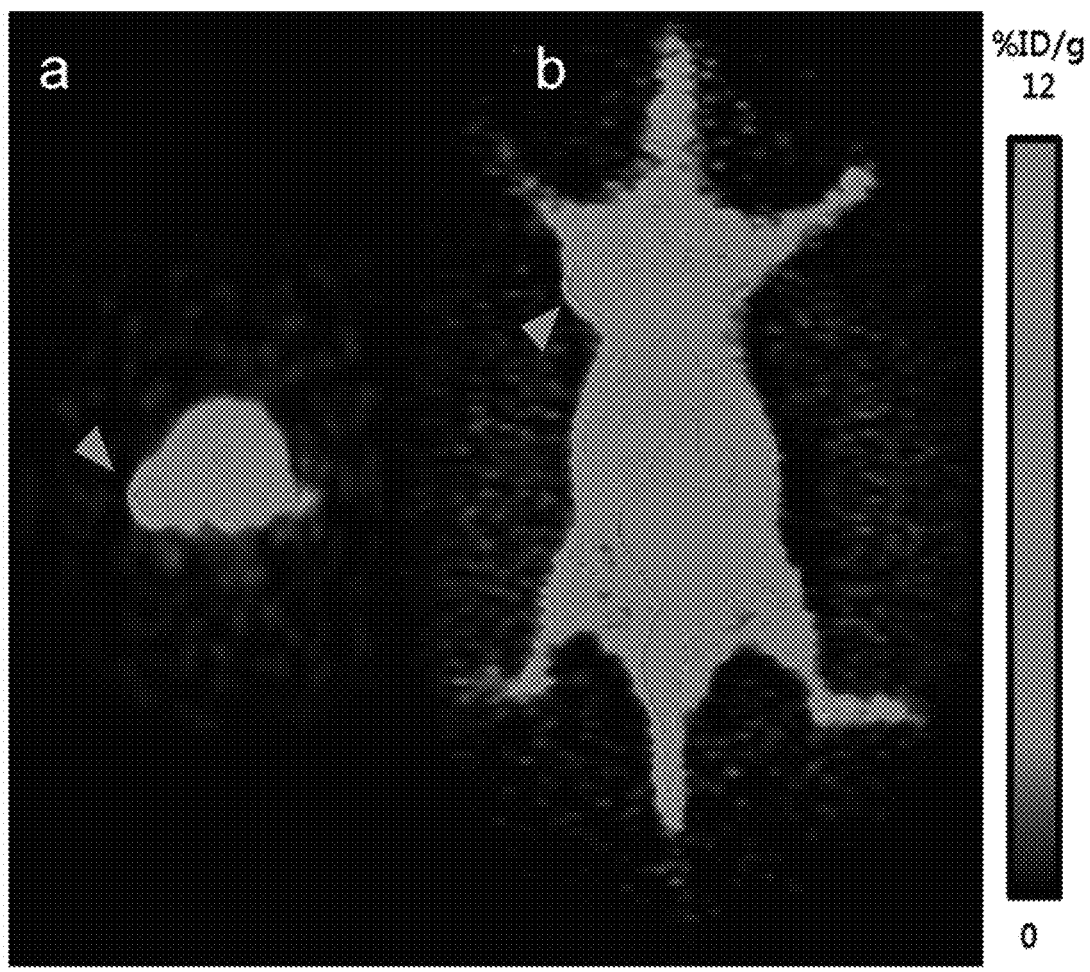

FIG. 17 illustrates in vivo PET images representing $^{18}$F-labeled ERBB2 aptamer {[AP001-25]-hy(bp)-L-$F^{18}$} in mice having BT474 cancer, wherein Hy(bp) indicates ODN/cODN hybridization as the hybridization (base pairing).

Figure 18:
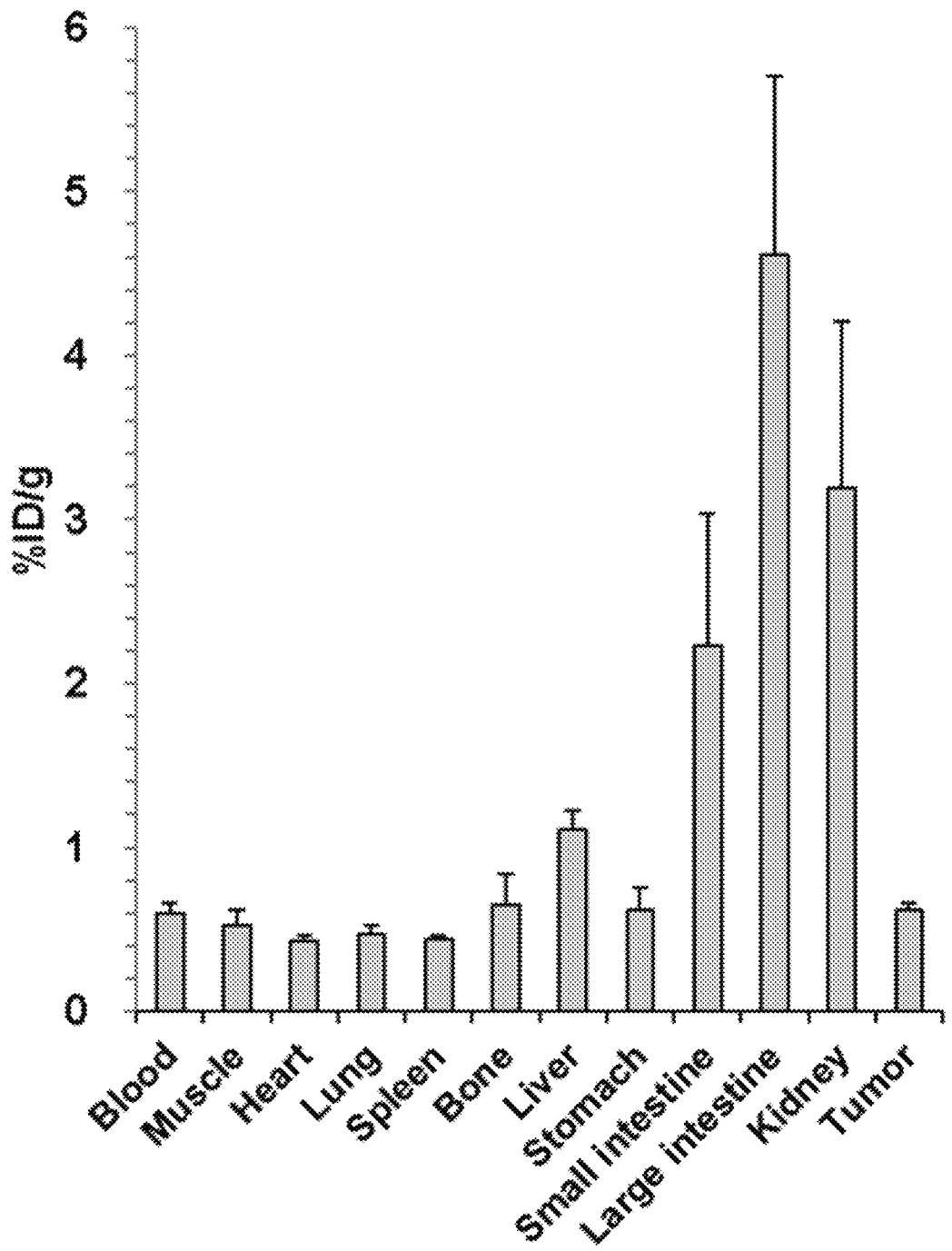

FIG. 18 illustrates studied results of in vivo distribution of $^{18}$F-labeled ERBB2 aptamer {[AP001-25]-hy(bp)-L-$F^{18}$} in mice having cancer, wherein data is given for active injection per gram of tissue by a percentage (% ID/g) (Error bars, SD (N=4)).

Figure 19A:
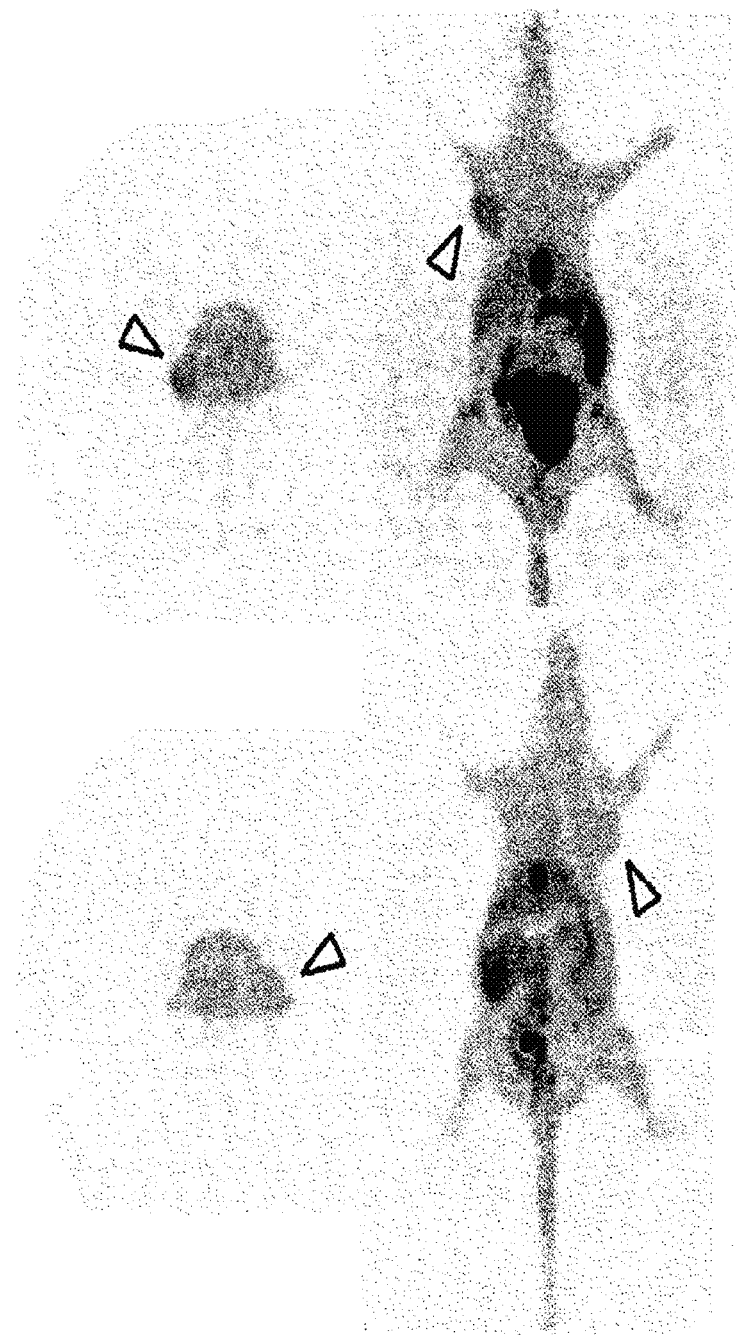
Figure 19B:
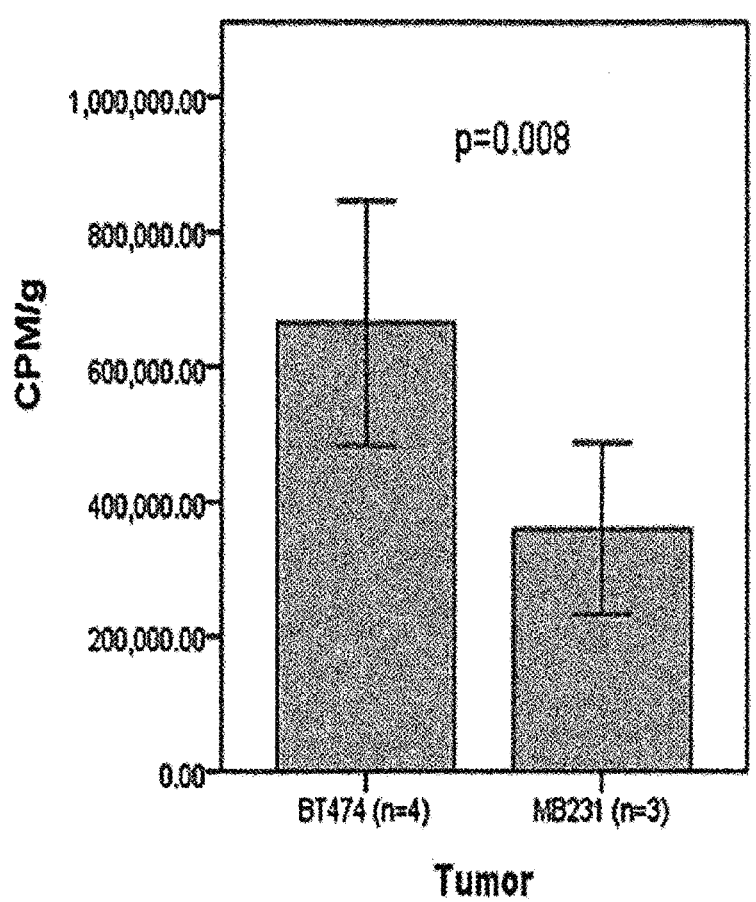
Figure 19C:
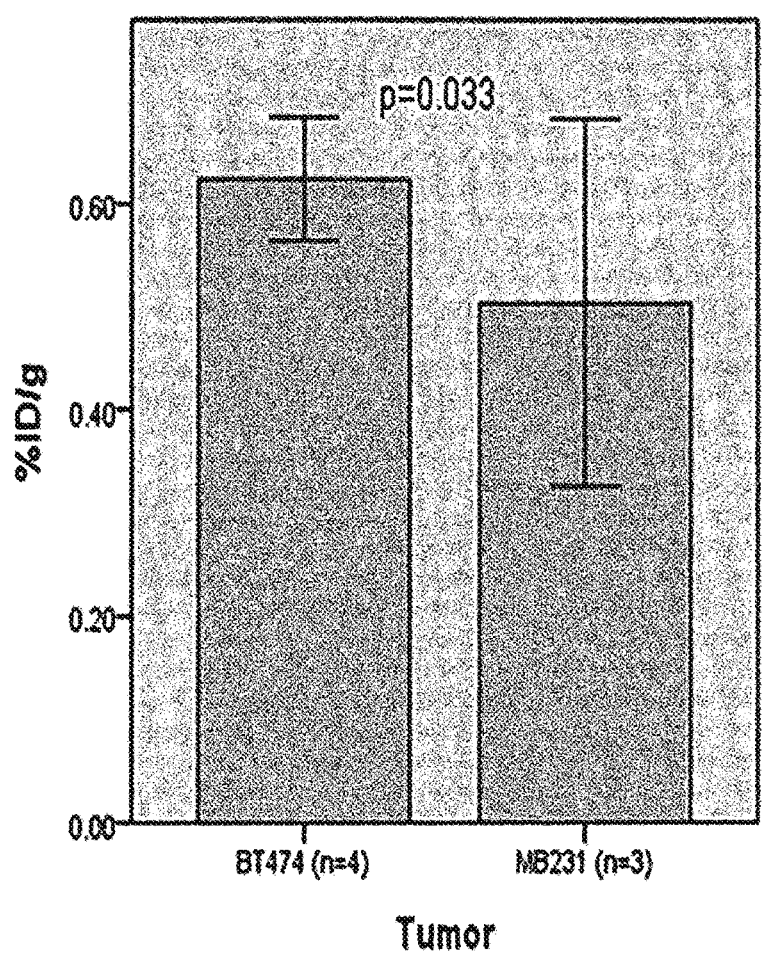

FIGS. 19A to 19C illustrate in vivo PET images representing $^{18}$F-labeled ERBB2 aptamer {[AP001-25]-hy(bp)-L-$F^{18}$} in mice having HER2-positive and negative cancers, respectively, in particular: (a) HER2 over-expressing BT474 cancer (left armpit); (b) HER2 negative MDA-MB231 cancer (right armpit) wherein (a) shows more increased intake than in (b); and (c) count per minute (CPM) and injection amount per gram (% ID/g) into tumor tissue are calculated with $^{18}$F-labeled ERBB2 aptamer.

FIG. 20 illustrates H&E and IHC staining of HER2 (original magnification 400×)

DETAILED DESCRIPTION

ERBB2 aptamer specifically bound to HER2 receptor in relevant to breast cancers, which is used in the present invention, has a DNA sequence of 5'-TCAGCCGCCAGCCAGTTC-[core sequence]-GACCAGAGCACCACAGAG-3' wherein the number '6' in the core sequence or 'n' in the attached DNA sequence listing represents NaptyldU.

TABLE 1

| | Description (clone number) | Core sequence |
|---|---|---|
| 1 | 9-ER-N-A01_A05 | A6G66AGAG666GCC6GAG6GCC6CG6AAGGGCG6AACAA (SEQ ID NO: 1) |
| 2 | 9-ER-N-A02_B05 | 6AC6GGGCCCG66AGCC6C6GGCGC6CC66CGC66G6GCC (SEQ ID NO: 2) |
| 3 | 9-ER-N-A03_C05 | 66A6CAACGCAC6GAGGGCG6CAGC66C66666AGG (SEQ ID NO: 3) |
| 4 | 9-ER-N-A04_D05 | A6G6AGAG666GCC6GAG6GCC6CGCAAGGGCG6AACAG (SEQ ID NO: 4) |
| 5 | 9-ER-N-A06_E05 | 6CC6G6CCCGG666ACACAAG66AAGGCAGCCGC6GGA6A (SEQ ID NO: 5) |
| 6 | 9-ER-N-B02_F05 | G6C6GAACACCGAGA66AGC6GAACGAACGG6A6GGACG6 (SEQ ID NO: 6) |
| 7 | 9-ER-N-B03_G05 | 6CC6GGCA6G66CGA6GGAGGCC666GA66ACAGCCCAGA (SEQ ID NO: 7) |
| 8 | 9-ER-N-B04_H05 | CGCGA66AGA6GAACGCACAA6ACCCG66C6GAG6AAAG6 (SEQ ID NO: 8) |
| 9 | 9-ER-N-B08_A06 | G6C6GAACACCGAGA66AGCCGAACGAACGG6A6GGACG6 (SEQ ID NO: 9) |

TABLE 1-continued

| | Description (clone number) | Core sequence |
|---|---|---|
| 10 | 9-ER-N-B09_B06 | G66AGAC6GAACGCAC6GAGGGCCGCAGCC6A6C6GAAGG (SEQ ID NO: 10) |
| 11 | 9-ER-N-B12_C06 | A6G66AGAG666GCC6GAG6GCC6CGCAAGGGCG6AACAA (SEQ ID NO: 11) |
| 12 | 9-ER-N-C02_D06 | 6CC6GGCA6G66CGA6GGAGGCC666GA66ACAGCCCAGA (SEQ ID NO: 7) |
| 13 | 9-ER-N-C03_E06 | G6C6GAGCA6CGCG666AGCCGAACGC6CGG6GAGG6AGA6 (SEQ ID NO: 12) |
| 14 | 9-ER-N-C05_F06 | 6CA6GGCA6G66CGA6GGAGGCC666GA66ACAGCCCAGA (SEQ ID NO: 13) |
| 15 | 9-ER-N-C06_G06 | C6ACACGAA6CAAC6CCCC6CCGCA6AC6GAACA6CACAA (SEQ ID NO: 14) |
| 16 | 9-ER-N-C08_H06 | 66AGCAAAA6GCCA6G6GCG6CC6G6CCCGG666ACAGC (SEQ ID NO: 15) |
| 17 | 9-ER-N-C10_A07 | 6GA6G6CCCCAAC6CAGC6G6GAA6C6A6GCCCCCGCCCA (SEQ ID NO: 16) |
| 18 | 9-ER-N-D01_B07 | C6GAGCGG66AC6ACACCACCG6GAGACC66AG66ACAAA (SEQ ID NO: 17) |
| 19 | 9-ER-N-D02_C07 | A66AGA6GAAAGCGCA66CCAACAACAGA6AA6C6GAGGG (SEQ ID NO: 18) |
| 20 | 9-ER-N-D03_D07 | 6CC6GGCA6G66CGA6GGAGGCC666GA66ACAGCCCAGA (SEQ ID NO: 7) |
| 21 | 9-ER-N-D04_E07 | 666GGAG6G6C66ACGG66GGAG6AA6CGAGGA6GGA6GA (SEQ ID NO: 19) |
| 22 | 9-ER-N-D05_F07 | CCG66ACC6ACC6CC6CGACCG6GGG6GCCC66AG6CCCA (SEQ ID NO: 20) |
| 23 | 9-ER-N-D06_G07 | 6CC6GGCA6G66CGA6GGAGGCC666GA66ACAGCCAGA (SEQ ID NO: 21) |
| 24 | 9-ER-N-D07_H07 | CCG66ACC6ACC6CC6CGACCG6GGG6GCC666AG6CCCA (SEQ ID NO: 22) |
| 25 | 9-ER-N-D09_A08 | A6G66AGAG666GCC6GAG6GCC6CGCAAGGGCG6AACAA (SEQ ID NO: 23) |
| 26 | 9-ER-N-D11_B08 | 6CC6GGCA6G66CGA6GGAGGCC666GA66ACAGCCCAG6 (SEQ ID NO: 24) |
| 27 | 9-ER-N-E02_C08 | CCG66ACC6ACC6CC6CGACCG6GGG6GCCC66AG6CCCA (SEQ ID NO: 20) |
| 28 | 9-ER-N-E04_D08 | A66AGA6GAAAGCACA66CCAACAACAGA6AA6C6GAGGG (SEQ ID NO: 25) |
| 29 | 9-ER-N-E09_E08 | 6CC6GGCA6G66CGA6GGAGGCC666GA66ACAGCCCAGA (SEQ ID NO: 7) |
| 30 | 9-ER-N-E11_F08 | A6G66AGAG666GCC6GAG6GCG6CGCAAGGGCG6AACAG (SEQ ID NO: 26) |
| 31 | 9-ER-N-E12_G08 | 6GAGAAGGGC6G6GCC66AC6CAAAA666GGGA6C6GAA (SEQ ID NO: 27) |
| 32 | 9-ER-N-F01_H08 | G66AGAC6GAACGCAC6GAGGGCCGCAGCC6A6C6GAAGG (SEQ ID NO: 10) |
| 33 | 9-ER-N-F02_A09 | G6C6GAACACCGAGA66AGCCGAACGAACGG6A6GGACG6 (SEQ ID NO: 9) |
| 34 | 9-ER-N-F03_B09 | G6C6GAACACCGAGA66AGCCGAACGAACGG6A6GGACG6 (SEQ ID NO: 9) |
| 35 | 9-ER-N-F04_C09 | G6C6GAACACCGAGA66AGCCGAACGAACGG6A6GGACG6 (SEQ ID NO: 9) |
| 36 | 9-ER-N-F05_D09 | 6CC6GG6A6G66CGA6GGAGGCC666GA66ACAGCCCAGA (SEQ ID NO: 28) |
| 37 | 9-ER-N-F08_E09 | 6AGA6C6C6GA66AGG6AGAACGCCC6AC6C6AACGGCAG (SEQ ID NO: 29) |
| 38 | 9-ER-N-F09_F09 | 6GAGAAGGGC6G6GCC66AC6CAAAA666GGGGA6C6GAA (SEQ ID NO: 30) |
| 39 | 9-ER-N-F11_G09 | 6GAGAAGGGC6G6GCC66AC6CAAAA666GGGGA6C6GAA (SEQ ID NO: 31) |
| 40 | 9-ER-N-G02_H09 | A66AGA6GAAAGCGCA66CCAACAACAGA6AA6C6GAGGG (SEQ ID NO: 18) |
| 41 | 9-ER-N-G03_A10 | G6C6GAACACCGAGA66AGCCGAACGAACGG6A6GGACG6 (SEQ ID NO: 9) |
| 42 | 9-ER-N-G04_B10 | CG6CC66GG6GAG666GGG6C6GAGCAGGAGCACG6GA6 (SEQ ID NO: 32) |
| 43 | 9-ER-N-G08_C10 | 6CC6GGCA6G66CGA6GGAGGCC666GA66ACAGCCCAGA (SEQ ID NO: 7) |
| 44 | 9-ER-N-G09_D10 | G6C6GAACACCGAGA66AGCCGAACGAACGG6A6GGACG6 (SEQ ID NO: 9) |
| 45 | 9-ER-N-H01_E10 | A66AGA6GAAAGCACA66CCAACAACAGA6AA6C6GAGGG (SEQ ID NO: 33) |
| 46 | 9-ER-N-H02_F10 | 6CC6GGCA6G66CGA6GGAGGCC666GA66ACAGCCCAGA (SEQ ID NO: 7) |
| 47 | 9-ER-N-H03_G10 | A66AGA6GAAAGCACA66CCAACAACAGA6AA6C6GAGGG (SEQ ID NO: 34) |
| 48 | 9-ER-N-H04_H10 | G66AGAC6GAACGCAC6GAGGGCCGCAGCC6A6C6GAAGG (SEQ ID NO: 10) |
| 49 | 9-ER-N-H08_A11 | 6CC6GGCA6G66CGA6GGAGGCC666GA66ACAGCCCAGA (SEQ ID NO: 7) |
| 50 | 9-ER-N-H09_B11 | A6G66AGAG6C6GCC6GAG6GCC6CGCAAGGGCG6AACAG (SEQ ID NO: 35) |

6=NapdU [5-(N-Naphthylcarboxyamide)-[0070] 2'-deoxyuridine]. In the present invention, HER2 aptamer labeled with a radioactive isotope ('radioisotope'), for example, $^{18}$F, $^{32}$P, $^{123}$I, $^{89}$Zr, $^{67}$Ga, $^{201}$Tl and $^{111}$In-111, or a fluorescent dye, for example, a cyanine fluorescent dye such as Cy3, Cy5, Cy7, etc. was utilized for in vivo imaging. In embodiments of the present invention, evaluation of target specificity for in vivo molecule imaging and potential clinical application have been performed using ERBB2 aptamer labeled with the radioisotope or fluorescent dye.

ERBB2 aptamer for a human epidermal growth factor receptor 2 (HER2) was labeled with $^{18}$F-fluoride isotope. In order to confirm that the aptamer entered HER2 expressed cancer cell line, the aptamer was compared with a control aptamer by flow cytometry and confocal microscope. The $^{18}$F-labeled HER2-specific ERBB2 aptamer was subjected to positron tomography thus to obtain biomolecular images of the mice transplanted with BT474 or KPL4 cells over time.

Hereinafter, the present invention will be described in detail.

Cell Culture

HER2 expressed human breast cancer cell lines, e.g., BT474, KPL4, N89 and SK-BR-3 were used for in vitro and in vivo experiments. Further, a human breast cancer cell line MDA-MB231 was used as a control group. All cell lines were purchased from ATCC and incubated and maintained in MEM medium containing 10% FBS.

Cell Lysis, Western Blot

In order to extract intracellular protein, a cell lysate including a protease inhibitor was incubated on ice for 30 minutes. The resulting cell lysate was purified by centrifugation at 4° C. for 20 minutes. For protein quantification, the cell lysate was quantified by Bradford method, followed by separation of 30 μg protein extract from the respective samples through electrophoresis using 10% SDS-PAGE. Then, the resulting product was transferred to a nitrocellulose membrane and subjected to photosensitization on x-ray film with ECL, using HER2 antibody and the control group, that is, a beta-action antibody as a probe.

ERBB2 Aptamer Synthesis

DNA sequences of HER2-(+) targeting ERBB2 aptamers are shown in Table 2 below.

TABLE 2

| Code # | Sequence (DNA) | Binding affinity [Kd] | Molecular weight (g/mole) |
|---|---|---|---|
| AP001-25 | [6CC6GGCA6G66CGA6GGAGGCC666GA66ACAG CCCAGA] | 0.94 nM | 14163.90 |
| AP001-24 | [A6G66AGAG666GCC6GAG6GCC6CGCAAGGGCG 6AACAA] | 3.10 nM | 14067.80 |
| [AP001-25]-ODN | [6CC6GGCA6G66CGA6GGAGGCC666GA66ACAGC CCAGA]CAGCCACACCACCAG | 3.40 nM | 18701.81 |
| [AP001-24]-ODN | [A6G66AGAG666GCC6GAG6GCC6CGCAAGGGCG 6AACAA]CAGCCACACCACCAG | 8.20 nM | 18605.71 |

6=NapdU [5-(N-Napthylcarboxyamide)-2'-deoxyuridine]
A=2'-deoxyAdenosine
G=2'-deoxyGuanosine
C=2'-deoxyCytidine
T=2'-deoxyThymidine (Thymidine)

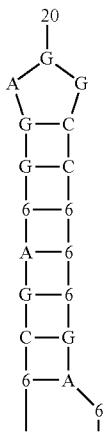

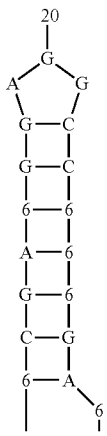

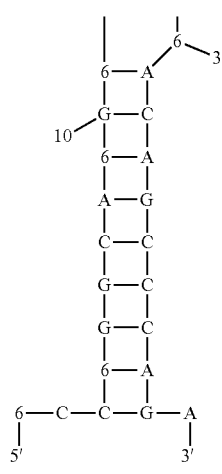
[AP001-35]
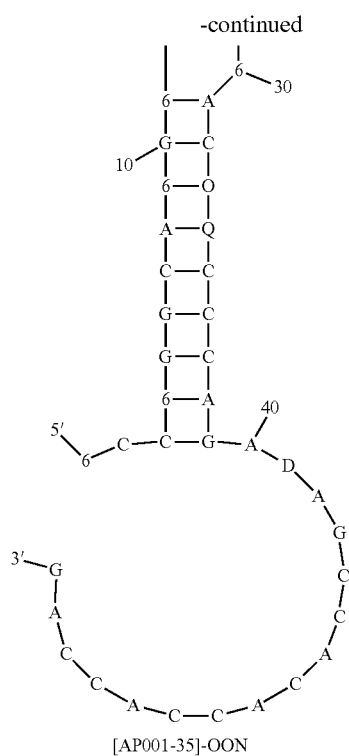
[AP001-35]-OON
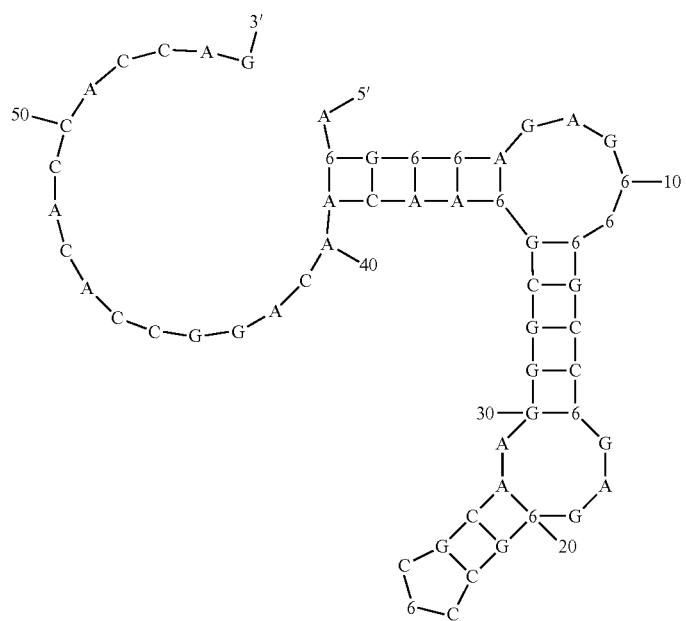
[AP001-34]-OON
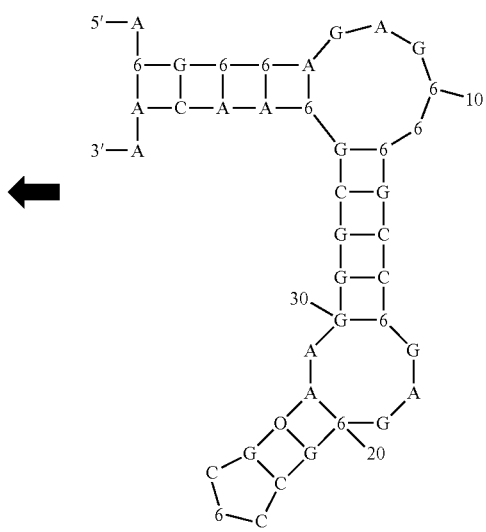
[AP001-34]

The RBB2 aptamers, in particular, AP001-24 has a binding affinity (Kd) of 3.1 nM to a target and AP001-25 has a binding affinity of 0.9 nM.

Herein, 6 denotes NapdU [5-(N-naphthylcarboxamide)-2'-deoxyuridine] represented by the following formula, A=2'-deoxyadenosine, G=2'-deoxyguanosine and C=2'-deoxycytidine.

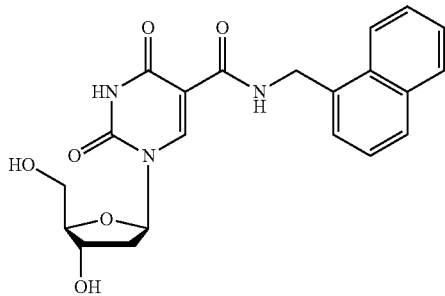

For aptamer hybridization, synthesis including a fully matching sequence, that is, ODN (5'-CAGCCACAC-CACCAG-3') (SEQ ID NO: 36) at 3' in each of the ERBB2 aptamers {[AP001-24] and [AP001-25]} was performed.

[AP001-24]-ODN Synthesis

5'-[6CC 6GG CA6 G66 CGA 6GG AGG CC6 66G A66 ACA GCC CAG A]-CAG CCA CAC CAC CAG-3' {[AP001-24]-ODN} was synthesized as follows.

Aptamer synthesis was performed by a solid phase synthesis process through phosphoramidite coupling reaction, and after the synthesis, the product was reacted in a t-butylamine:methanol:water (1:1:2 v/v/v) solution at 70° C. for 5 hours, thus to obtain a complete aptamer through cleavage and deprotection processes, followed by drying the same. The synthesized aptamer was isolated by HPLC [C18 column (Waters, Xbridge OST C18 10×50 mm, 260 nm] and then was subjected to measurement of a molecular weight by means of ESI MS mass spectrometer (Qtrap2000, ABI).

$11^{th}$ aptamer in Table 1 (SEQ ID NO: 11) corresponds to AP001-24.

[AP001-25]-ODN Synthesis:

5'-[A6G 66A GAG 666 GCC 6GA G6G CC6 CGC AAG GGC G6A ACA A]-CAG CCA CAC CAC CAG-3' {[AP001-25]-ODN} was synthesized by the same synthesis procedures as described in the above section for {[AP001-24]-ODN} synthesis.

$12^{th}$ aptamer in Table 1 (SEQ ID NO: 7) corresponds to AP001-25.

In the same manner, each of aptamers, that is, CAG-3' {each of aptamers (SEQ ID NOs: 1-35) in Table 1-ODN} was synthesized by the same procedures as described in the above section for {[AP001-24]-ODN} synthesis.

[AP001-24]-ODN-idT Synthesis:

5'-[6CC 6GG CA6 G66 CGA 6GG AGG CC6 66G A66 ACA GCC CAG A]-CAG CCA CAC CAC CAG-idT-3' {[AP001-24]-ODN-idT} was synthesized using idT (invert dT) CPG (Glen, 20-0302-10) by the same procedures as described in the above section for {[AP001-24]-ODN} synthesis.

[AP001-25]-ODN-idT Synthesis:

5'-[A6G 66A GAG 666 GCC 6GA G6G CC6 CGC AAG GGC G6A ACA A]-CAG CCA CAC CAC CAG-idT-3' {[AP001-25]-ODN-idT} was synthesized using idT CPG (Glen, 20-0302-10) by the same procedures as described in the above section for {[AP001-24]-ODN} synthesis.

Cholesteryl-[AP001-24]-ODN Synthesis:

5'-cholesteryl-[6CC 6GG CA6 G66 CGA 6GG AGG CC6 66G A66 ACA GCC CAG A]-CAG CCA CAC CAC CAG-3' {cholesteryl-[AP001-24]-ODN} was synthesized using cholesterol-PA (Glen, 10-1976-90) by the same procedures as described in the above section for {[AP001-24]-ODN} synthesis.

Cholesteryl-[AP001-25]-ODN Synthesis:

5'-cholesteryl-[A6G 66A GAG 666 GCC 6GA G6G CC6 CGC AAG GGC G6A ACA A]-CAG CCA CAC CAC CAG-3' {cholesteryl-[AP001-25]-ODN} was synthesized using cholesterol-PA (Glen, 10-1976-90) by the same procedures as described in the above section for {[AP001-24]-ODN} synthesis.

Cholesteryl-[AP001-24]-ODN-idT Synthesis:

5'-cholesteryl-[6CC 6GG CA6 G66 CGA 6GG AGG CC6 66G A66 ACA GCC CAG A]-CAG CCA CAC CAC CAG-idT-3' {cholesteryl-[AP001-24]-ODN-idT} was synthesized using idT CPG (Glen, 20-0302-10) and cholesterol-PA (Glen, 10-1976-90) by the same procedures as described in the above section for {[AP001-24]-ODN} synthesis.

Cholesteryl-[AP001-25]-ODN-idT Synthesis:

5'-cholesteryl [A6G 66A GAG 666 GCC 6GA G6G CC6 CGC AAG GGC G6A ACA A]-CAG CCA CAC CAC CAG-idT-3' {cholesteryl-[AP001-25]-ODN-idT} was synthesized using idT CPG (Glen, 20-0302-10) and cholesterol-PA (Glen, 10-1976-90) by the same procedures as described in the above section for {[AP001-24]-ODN} synthesis.

PEGylated-[AP001-24]-ODN Synthesis:

5'-PEGylated-[6CC 6GG CA6 G66 CGA 6GG AGG CC6 66G A66 ACA GCC CAG A]-CAG CCA CAC CAC CAG' {PEGylated-[AP001-24]-ODN} was synthesized using polyethyleneglycol 2000 CED PA (ChemGenes, CLP-2119) by the same procedures as described in the above section for {[AP001-24]-ODN} synthesis.

PEGylated-[AP001-25]-ODN Synthesis:

5'-PEGylated-[A6G 66A GAG 666 GCC 6GA G6G CC6 CGC AAG GGC G6A ACA A]-CAG CCA CAC CAC CAG-3' {PEGylated-[AP001-25]-ODN} was synthesized using polyethyleneglycol 2000 CED PA (ChemGenes, CLP-2119) by the same procedures as described in the above section for {[AP001-24]-ODN} synthesis.

PEGylated-[AP001-24]-ODN-idT Synthesis:

5'-PEGylated-[6CC 6GG CA6 G66 CGA 6GG AGG CC6 66G A66 ACA GCC CAG A]-CAG CCA CAC CAC CAG-idT-3' {PEGylated-[AP001-24]-ODN-idT} was synthesized using idT CPG (Glen, 20-0302-10) and polyethyleneglycol 2000 CED PA (ChemGenes, CLP-2119) by the same procedures as described in the above section for {[AP001-24]-ODN} synthesis.

PEGylated-[AP001-25]-ODN-idT Synthesis:

5'-PEGylated-[A6G 66A GAG 666 GCC 6GA G6G CC6 CGC AAG GGC G6A ACA A]-CAG CCA CAC CAC CAG-3' {PEGylated-[AP001-25]-ODN-idT} was synthesized using idT CPG (Glen, 20-0302-10) and polyethyleneglycol 2000 CED PA (ChemGenes, CLP-2119) by the same procedures as described in the above section for {[AP001-24]-ODN} synthesis.

Cy5 Conjugated cODN (Complementary Oligonucleotide)[cODN-Cy5] Synthesis:

The following figure represents structures of cODN-Cy5 and cODN-L-F$^{18}$ (L=linker) and synthesis thereof.

3'-GTCGGTGTGGTGGTC-Cy5-5' (SEQ ID NO: 37)

cODN-Cy5

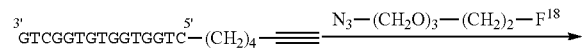

(SEQ ID NO: 37)

cODN-Hexynyl

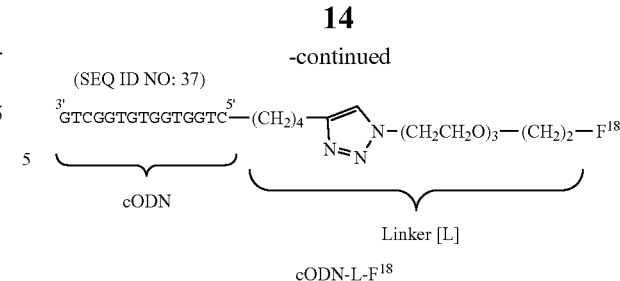

cODN-L-F$^{18}$

5'-Cy5-[CTGGTGGTGTGGCTG]-3' (SEQ ID NO: 37) [cODN-Cy5] was synthesized using Cy5-PA (Glen, 10-5915-10) by the same procedures as described in the above section for {[AP001-24]-ODN} synthesis.

Formation of cy5-Labeled ERBB2 Aptamer

Table 3 below shows a hybridization structure of R-[ERBB2 aptamer]-ODN-X (R=H, cholesterol or PEG, and X=H or idT) and cODN-Cy5, which is represented by [ERBB2 aptamer]-X-hy(bp)-Cy5.

TABLE 3

| R-[ERBB2 aptamer]-X-hy(bp)-Cy5 | Hybridizatin Sequence R-[ERBB2 aptamer]-X-hy(bp)-Cy5 |
|---|---|
| [AP001-25]-hy(bp)-Cy5 | 3'-GTC CGT GTG GTG GTC-Cy5-5'<br>5'-[6CC 6GG CA6 G66 CGA 6GG AGG CC6 66G A66 ACA GCC CAG A]-CAG CCA CAC CAC CAG-3' |
| [AP001-25]-idT-hy(bp)-Cy5 | 3'-GTC CGT GTG GTG GTC-Cy5-5'<br>5'-[6CC 6GG CA6 G66 CGA 6GG AGG CC6 66G A66 ACA GCC CAG A]-CAG CCA CAC CAC CAG-idT-3' |
| Cholesteryl-[AP001-25]-hy(bp)-Cy5 | 3'-GTC CGT GTG GTG GTC-Cy5-5'<br>5'-Chol-[6CC 6GG CA6 G66 CGA 6GG AGG CC6 66G A66 ACA GCC CAG A]-CAG CCA CAC CAC CAG-3' |
| Cholesteryl-[AP001-25]-idT-hy(bp)-Cy5 | 3'-GTC CGT GTG GTG GTC-Cy5-5'<br>5'-Chol-[6CC 6GG CA6 G66 CGA 6GG AGG CC6 66G A66 ACA GCC CAG A]-CAG CCA CAC CAC CAG-idT-3' |
| PEGylated-[AP001-25]-hy(bp)-Cy5 | 3'-GTC CGT GTG GTG GTC-Cy5-5'<br>5'-PEG-[6CC 6GG CA6 G66 CGA 6GG AGG CC6 66G A66 ACA GCC CAG A]-CAG CCA CAC CAC CAG-3' |
| PEGylated-[AP001-25]-idT-hy(bp)-Cy5 | 3'-GTC CGT GTG GTG GTC-Cy5-5'<br>5'-PEG-[6CC 6GG CA6 G66 CGA 6GG AGG CC6 66G A66 ACA GCC CAG A]-CAG CCA CAC CAC CAG-idT-3' |
| [AP001-24]-hy(bp)-Cy5 | 3'-GTC CGT GTG GTG GTC-Cy5-5'<br>5'-[A6G 66A GAG 666 GCC 6GA G6G CC6 CGC AAG GGC G6A ACAA]-CAG CCA CAC CAC CAG-3' |
| [AP001-24]-idT-hy(bp)-Cy5 | 3'-GTC CGT GTG GTG GTC-Cy5-5'<br>5'-[A6G 66A GAG 666 GCC 6GA G6G CC6 CGC AAG GGC G6A ACAA]-CAG CCA CAC CAC CAG-idT-3' |
| Cholesteryl-[AP001-24]-hy(bp)-Cy5 | 3'-GTC CGT GTG GTG GTC-Cy5-5'<br>5'-Chol-[A6G 66A GAG 666 GCC 6GA G6G CC6 CGC AAG GGC G6A ACAA]-CAG CCA CAC CAC CAG-3' |
| Cholesteryl-[AP001-24]-idT-hy(bp)-Cy5 | 3'-GTC CGT GTG GTG GTC-Cy5-5'<br>5'-Chol-[A6G 66A GAG 666 GCC 6GA G6G CC6 CGC AAG GGC G6A ACAA]-CAG CCA CAC CAC CAG-idT-3' |
| PEGylated-[AP001-24]-hy(bp)-Cy5 | 3'-GTC CGT GTG GTG GTC-Cy5-5'<br>5'-PEG-[A6G 66A GAG 666 GCC 6GA G6G CC6 CGC AAG GGC G6A ACAA]-CAG CCA CAC CAC CAG-3' |

TABLE 3-continued

| R-[ERBB2 aptamer]-X-hy(bp)-Cy5 | Hybridizatin Sequence R-[ERBB2 aptamer]-X-hy(bp)-Cy5 |
|---|---|
| PEGylated-[AP001-24]-idT-hy(bp)-Cy5 | 3'-GTC CGT GTG GTG GTC-Cy5-5'<br>5'-PEG-[A6G 66A GAG 666 GCC 6GA G6G CC6 CGC AAG GGC G6A ACAA]-CAG CCA CAC CAC CAG-idT-3' |

The Cy5-labeled ERBB2 aptamer, that is, {R-[ERBB2 aptamer]-X-hy(bp)-Cy5} was prepared in the following manner.

Figure 1:
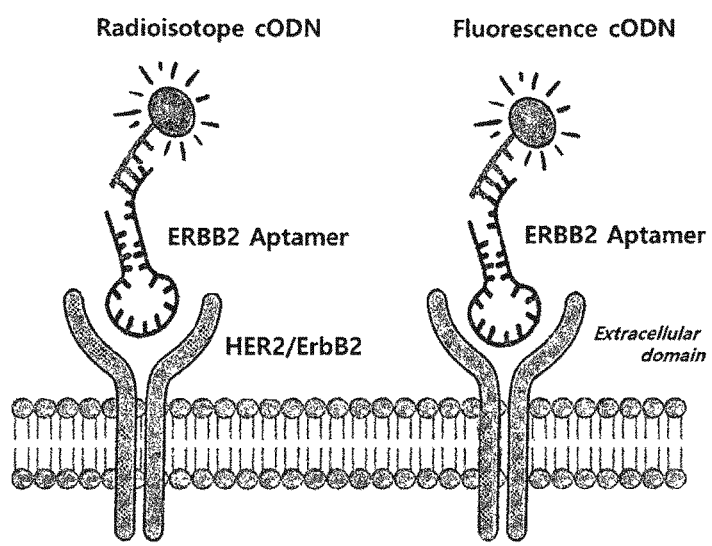
FIG. 1 is a schematic diagram illustrating a mechanism of radiation or fluorescence-labeled ERBB2 aptamer.
Figure 2:
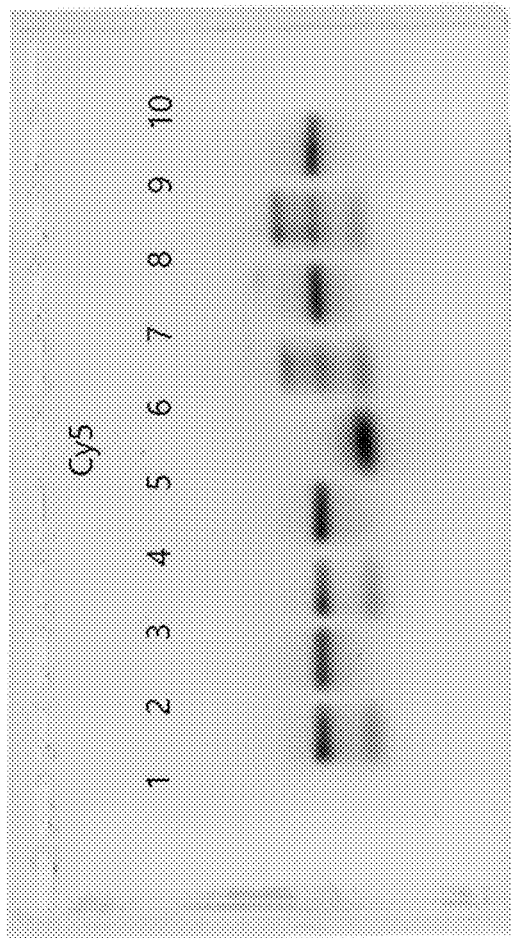
FIG. 2 illustrates analyzed results of R-[ERBB2 aptamer]-X-hy(bp)-Cy5, which is a product obtained by hybridization of R-[ERBB2 aptamer]-ODN-X (R=H, cholesterol or PEG, and X=H or idT) with cODN-Cy5, using Typhoon FLA 7000 3% agarose gel.

First, cODN-Cy5 and [ERBB2 aptamer]-ODN in equal moles were put in an annealing buffer (PBS). Herein, a concentration of $MgCl_2$ was controlled to reach a final concentration of 10 mM. This reaction product was left at 95° C. for 5 minutes, and then slowly cooled at room temperature. Hybridization efficiency of cODN-Cy5 and [ERBB2 aptamer]-ODN was assessed by electrophoresis (Typhoon FLA 7000 3% agarose gel analysis) and HPLC (XBridge OST analytical column (2.5 µm, 4.6×50 mm, Waters, 254 nm, 0.1M TEAA/acetonitrile). FIG. 2 shows analyzed results of R-[ERBB2 aptamer]-X-hy(bp)-Cy5 as a resulting product of hybridization of [ERBB2 aptamer]-ODN-X (R=H, cholesterol or PEG, and X=OH or idT) and cODN-Cy5, using Typhoon FLA 7000 3% agarose gel.

Figure 3:
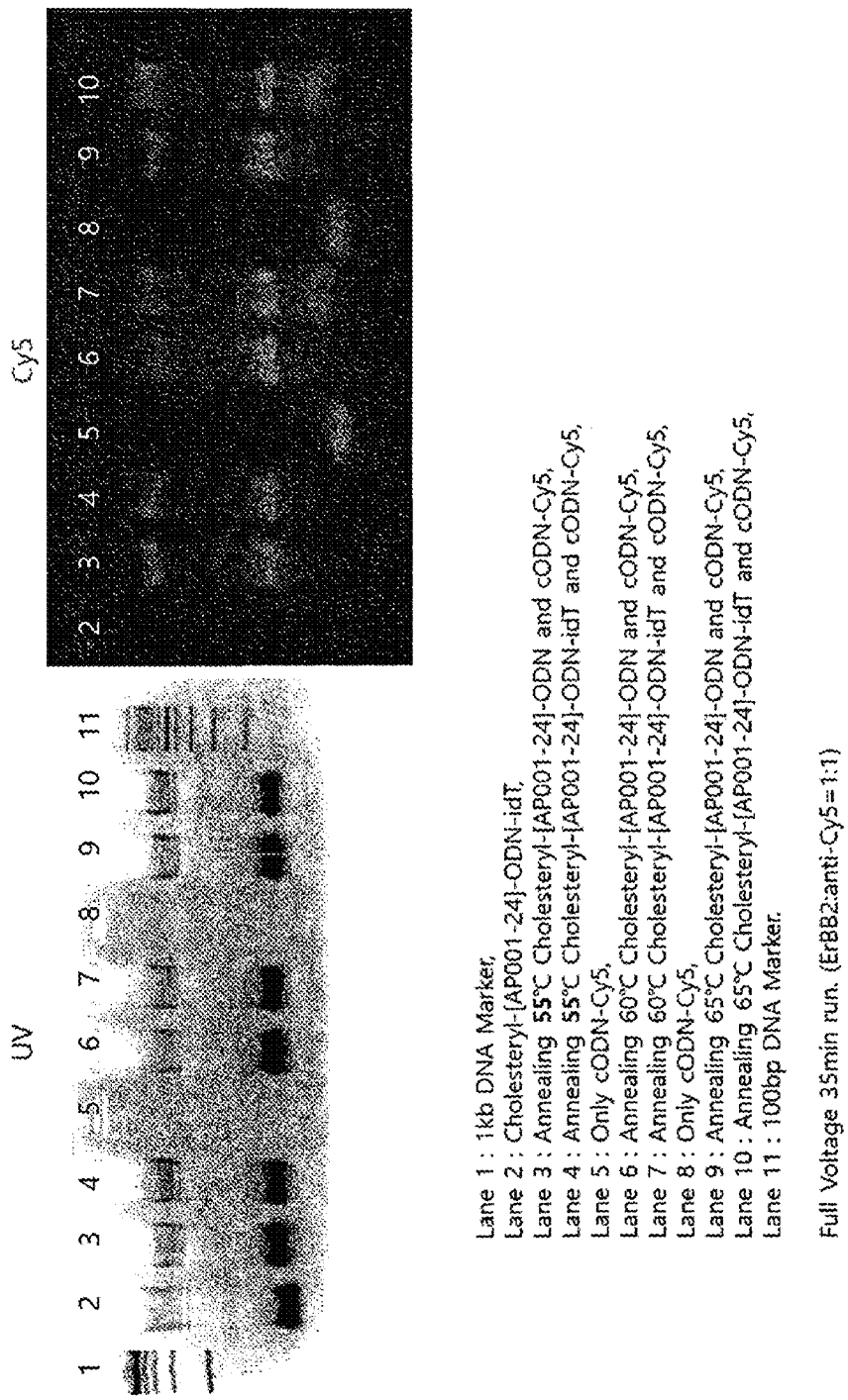
FIG. 3 illustrates results of identifying the complementary base pairing between cholesteryl-[AP001-24]-ODN-idT or cholesteryl-[AP001-24]-ODN aptamer and fluorescence-labeled cODN (cODN-Cy5), using 3% agarose gel at 50, 55 and 60° C. (black: aptamer, and red: cODN-Cy5).
Figure 4:
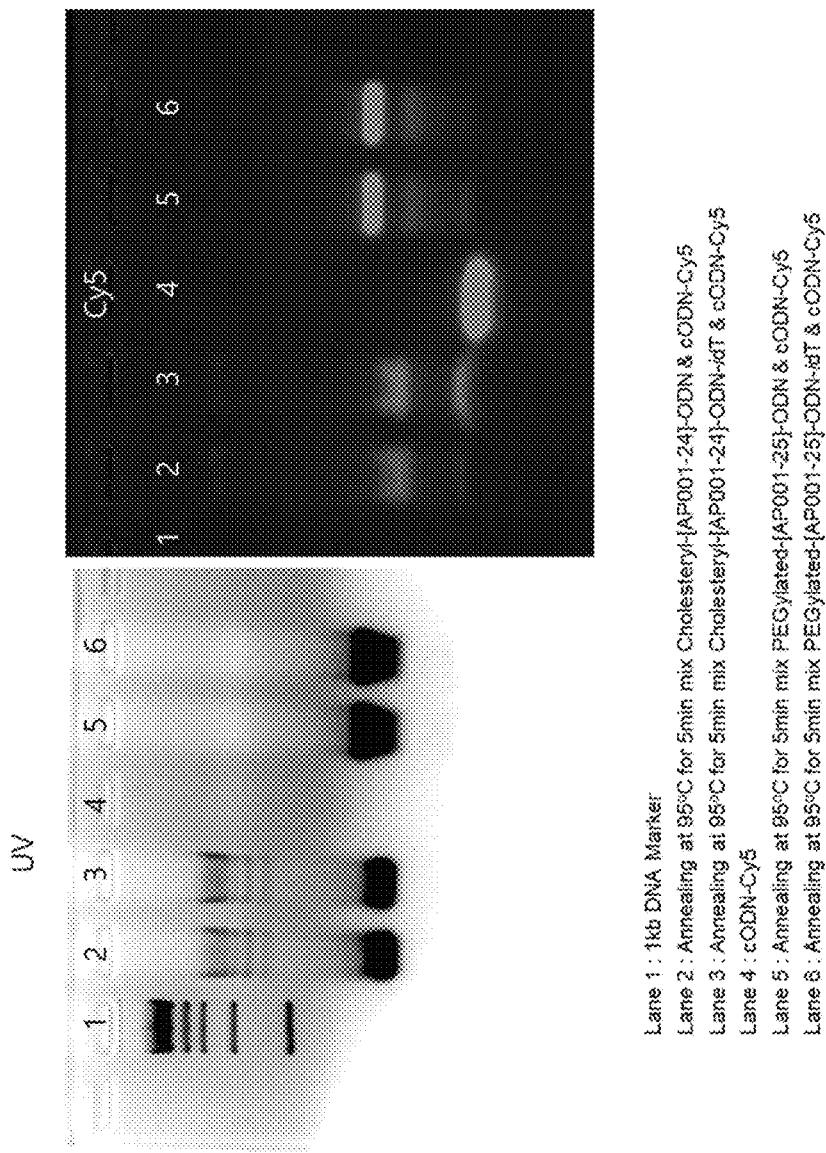
FIG. 4 illustrates results of identifying the complementary base pairing between cholesteryl-[AP001-24]-ODN-idT, cholesteryl-[AP001-24]-ODN, PEGylated-[AP001-25]-ODN-idT or PEGylated-[AP001-25]-ODN aptamer and fluorescence-labeled cODN (cODN-Cy5), which were heated to 95° C., using agarose gel.

Complementary base pairing between a synthetic oligonucleotide labeled with a fluorescent dye, that is, Cy5 (cODN-Cy5), and [ERBB2 aptamer]-ODN, was assessed. After mixing cholesteryl-[AP001-24]-ODN-idT or cholesteryl-[AP001-24]-ODN and cODN-Cy5 in 1:1 ratio, a temperature was maintained so that these components are bound together at 55, 60 and 65° C. In order to confirm the binding, electrophoresis was conducted in 3% agarose gel, followed by fluorescent imaging Cy5 through FLA 5000. Then, the entire aptamer was stained with EtBr and was subjected to UV imaging. The results are shown in FIG. 3. In order to compare the complementary base pairing between cholesteryl-[AP001-24]-ODN-idT, cholesteryl-[AP001-24]-ODN, PEGylated-[AP001-25]-ODN-idT or PEGylated-[AP001-25]-ODN and cODN-Cy5, each of these aptamers was mixed with cODN-Cy5 in 1:1 ratio and heated at 95° C. for 5 minutes to bind together, followed by assessment of the binding in the same manner as described above. The complementary base pairings between cholesteryl-[AP001-24]-ODN-idT, cholesteryl-[AP001-24]-ODN, PEGylated-[AP001-25]-ODN-idT or PEGylated-[AP001-25]-ODN and cODN-Cy5 with or without heating at 95° C., were determined and compared to each other. The comparison results are show in FIG. 4.

Formation of $F^{18}$ Radioisotope-Labeled cODN (Complementary Oligonucleotide) [cODN-L-$F^{18}$]

Synthesis of $^{18}$F-labeled cODN was performed on the basis of the process already reported in the art (see reference 24). After generating no-carrier-added 18F-fluoride ions in a synthesis device (Tracerlab FXFN, GE Healthcare, Milwaukee, Wis., USA) and reacting the same with mesylate (at 100° C. for 10 minutes), $^{18}$F-fluoro-PEG-azide (18F-FPA) was purified by using HPLC. After adding 1M N,N-disopropyl ethylamine in acetonitrile (10 mL) and 100 mM copper iodide (I) in acetonitrile (20 mL) to 5'-hexynyl complementary oligonucleotide (5'-hex-cODN; 200 mg), 18F-FPA (750e 1100 MBq) was further added thereto, followed by click chemistry reaction (at 70° C. for 20 minutes). The synthesized $^{18}$F-labeled cODN (cODN-L-$F^{18}$) was purified by using HPLC H (Xbridge OST C18 10×50 mm, an eluent of acetonitrile/0.1M TEAA in 5:95 to 95:5 over 20 minutes, flow rate: 5 mL/min, and UV (254 nm)).

Formation of $F^{18}$ Radioisotope-Labeled ERBB2 Aptamer {R-[ERBB2 Aptamer]-X-hy(bp)-L-$F^{18}$]

Table 4 below shows a hybridization structure of R-[ERBB2 aptamer]-ODN-X (R=H, cholesterol or PEG, and X=OH or idT) and cODN-L-$F^{18}$ (L=lnker), which is represented by [ERBB2 aptamer]-X-hy(bp)-L-$F^{18}$.

TABLE 4

| R-[ERBB2 aptamer]-X-hy(bp)-Cy5 | Hybridizatin Sequence R-[ERBB2 aptamer]-X-hy(bp)-Cy5 |
|---|---|
| [AP001-25]-hy(bp)-L-$F^{18}$ | 3'-GTC CGT GTG GTG GTC-L-$F^{18}$-5'<br>5'-[6CC 6GG CA6 G66 CGA 6GG AGG CC6 66G A66 ACA GCC CAG A]-CAG CCA CAC CAC CAG-3' |
| [AP001-25]-idT-hy(bp)-L-$F^{18}$ | 3'-GTC CGT GTG GTG GTC-L-$F^{18}$-5'<br>5'-[6CC 6GG CA6 G66 CGA 6GG AGG CC6 66G A66 ACA GCC CAG A]-CAG CCA CAC CAC CAG-idT-3' |
| Cholesteryl-[AP001-25]-hy(bp)-L-$F^{18}$ | 3'-GTC CGT GTG GTG GTC-L-$F^{18}$-5'<br>5'-Chol-[6CC 6GG CA6 G66 CGA 6GG AGG CC6 66G A66 ACA GCC CAG A]-CAG CCA CAC CAC CAG-3' |
| Cholesteryl-[AP001-25]-idT-hy(bp)-L-$F^{18}$ | 3'-GTC CGT GTG GTG GTC-L-$F^{18}$-5'<br>5'-Chol-[6CC 6GG CA6 G66 CGA 6GG AGG CC6 66G A66 ACA GCC CAG A]-CAG CCA CAC CAC CAG-idT-3' |
| PEGylated-[AP001-25]-hy(bp)-L-$F^{18}$ | 3'-GTC CGT GTG GTG GTC-L-$F^{18}$-5'<br>5'-PEG-[6CC 6GG CA6 G66 CGA 6GG AGG CC6 66G A66 ACA GCC CAG A]-CAG CCA CAC CAC CAG-3' |
| PEGylated-[AP001-25]-idT-hy(bp)-L-$F^{18}$ | 3'-GTC CGT GTG GTG GTC-L-$F^{18}$-5'<br>5'-PEG-[6CC 6GG CA6 G66 CGA 6GG AGG CC6 66G A66 ACA GCC CAG A]-CAG CCA CAC CAC CAG-idT-3' |

TABLE 4-continued

| R-[ERBB2 aptamer]-X-hy(bp)-Cy5 | Hybridizatin Sequence R-[ERBB2 aptamer]-X-hy(bp)-Cy5 |
|---|---|
| [AP001-24]-hy(bp)-L-$F^{18}$ | 3'-GTC CGT GTG GTG GTC-L-$F^{18}$-5'<br>5'-[A6G 66A GAG 666 GCC 6GA G6G CC6 CGC AAG GGC G6A ACAA]-CAG CCA CAC CAC CAG-3' |
| [AP001-24]-idT-hy(bp)-L-$F^{18}$ | 3'-GTC CGT GTG GTG GTC-L-$F^{18}$-5'<br>5'-[A6G 66A GAG 666 GCC 6GA G6G CC6 CGC AAG GGC G6A ACAA]-CAG CCA CAC CAC CAG-idT-3' |
| Cholesteryl-[AP001-24]-hy(bp)-L-$F^{18}$ | 3'-GTC CGT GTG GTG GTC-L-$F^{18}$-5'<br>5'-Chol-[A6G 66A GAG 666 GCC 6GA G6G CC6 CGC AAG GGC G6A ACAA]-CAG CCA CAC CAC CAG-3' |
| Cholesteryl-[AP001-24]-idT-hy(bp)-L-$F^{18}$ | 3'-GTC CGT GTG GTG GTC-L-$F^{18}$-5'<br>5'-Chol-[A6G 66A GAG 666 GCC 6GA G6G CC6 CGC AAG GGC G6A ACAA]-CAG CCA CAC CAC CAG-idT-3' |
| PEGylated-[AP001-24]-hy(bp)-L-$F^{18}$ | 3'-GTC CGT GTG GTG GTC-L-$F^{18}$-5'<br>5'-PEG-[A6G 66A GAG 666 GCC 6GA G6G CC6 CGC AAG GGC G6A ACAA]-CAG CCA CAC CAC CAG-3' |
| PEGylated-[AP001-24]-idT-hy(bp)-L-$F^{18}$ | 3'-GTC CGT GTG GTG GTC-L-$F^{18}$-5'<br>5'-PEG-[A6G 66A GAG 666 GCC 6GA G6G CC6 CGC AAG GGC G6A ACAA]-CAG CCA CAC CAC CAG-idT-3' |

$F^{18}$ radioisotope-labeled ERBB2 aptamer, {R-[ERBB2 aptamer]-X-hy(bp)-L-$F^{18}$} was prepared in the following manner.

First, cODN-L-$F^{18}$ and [ERBB2 aptamer]-ODN in equal moles were put in an annealing buffer (PBS). Herein, a concentration of $MgCl_2$ was controlled to reach a final concentration of 10 mM. This reaction product was left at 95° C. for 5 minutes, and then slowly cooled at room temperature. Hybridization efficiency of cODN-L-$F^{18}$ and [ERBB2 aptamer]-ODN was assessed by using HPLC (XBridge OST analytical column (2.5 μm, 4.6×50 mm, Waters, 254 nm, 0.1M TEAA/acetonitrile). These products were combined at a hybridization rate of 98% or more.

Confocal Microscope

BT474, KPL4, N87, SK-BR-3 and MDA-MB231 cell lines were dispensed on a coverslip and incubated overnight. When about 80% of the cell lines were grown, the grown cells were carefully washed and incubated by treatment using fluorescence-labeled ERBB2 aptamer {R-[ERBB2 aptamer]-hy(bp)-Cy5} at a concentration of 250 mM. After culture, the product was carefully washed, followed by loading a culture medium containing DAPI on a slide. Then, florescence thereof was observed by an LSM 700 confocal microscope. Microscope setting was performed as follows: a 488 laser was used for FITC observation; excitation and emission were observed using BP490-555; a 639 laser was used for Texas red; and emission was observed using an LP640 filter.

In the same manner as the previous experiments, ERBB2 over-expressing breast cancer cell lines, e.g., KPL4, N87 and SK-BR-3 were dispensed on a coverslip and incubated overnight. When about 80% of the cell lines were grown, the grown cells were carefully washed and incubated by treatment using a sample prepared of Cy5 fluorescence-labeled ODN bound to ERBB2 aptamer using complementary base pairing. After culture, the product was carefully washed, followed by loading a culture medium containing DAPI on a slide. Then, florescence was observed by an LSM 700 confocal microscope.

The observed results are shown in FIG. 5.

Flow Cytometry

Specificity of ERBB2 aptamer was verified by a fluorescence activated cell separation method using a flow cytometry system (BD Biosciences). Appropriate numbers of BT474, KPL4, N87, SK-BR-3 or MDA-MB231 cancer cell lines were sub-cultured on a Petri-dish to grow the same to about 80%. The grown cells were treated with trypsin and washed with PBS, followed by binding fluorescence-labeled ODN to ERBB2 aptamer through a complementary base generated according to a temperature. The cells were treated with the binding-completed sample. Both of the ERBB2 aptamer {R-[ERBB2 aptamer]-hy(bp)-Cy5} and the control group, that is, 1% FES containing antibody were treated at 4° C. for 30 minutes, respectively. The completely treated sample was washed, followed by measurement and analysis of the bound ERBB2 aptamer by a fluorescence activated cell separation method.

Results of the above measurement and analysis are shown in FIGS. 6A to 6B.

In Vivo Experiments

17ββ-estradiol pellets were subcutaneously implanted into a side region of the neck of a 4 week-old Balb/c nude mouse so that estrogen is released in a sufficient amount to potentially induce a cancer. A few days later, BT474 or KPL4 human breast cancer cell line was subcutaneously implanted in 7×10⁶ cells per mouse. After allowing the cancer to develop for 3 weeks, cancer growth was measured using a caliper.

Into the right shoulder of Balb/C nude mouse, KPL4 cells as the human breast cancer cell line were subcutaneously implanted in 1×10⁵ cells per mouse. Thereafter, occurrence of cancer was induced.

PET Imaging of $F^{18}$ Radioisotope-Labeled ERBB2 Aptamer $F^{18}$ radioisotope-labeled ERBB2 aptamer was injected to a mouse, and after 60 minutes, static images were obtained by Inveron microPET scanner (Siemens, Knoxville, Tenn., USA) for 10 minutes. For $F^{18}$ radioisotope-labeled ERBB2 aptamer injection, the mouse was breathing anesthetized with 2% Isoflurane, followed by 7.4 MBq of $F^{18}$ radioisotope-labeled ERBB2 aptamer injection into a tail vein. The obtained listmode data is converted into synogram and re-configured by 3D Ordered Subset Expectation Maximization (OSEM) algorithm, followed by assessment using ASIpro (Concord Microsystems Inc., Knoxville, Tenn.).

After intravenous injection of $F^{18}$ radioisotope-labeled ERBB2 aptamer to a mouse having tumor grown by injection of human breast tumor cells, PET was executed using inveon PET of Siemens (Knoxville, Tenn.). The injected amount was 13.7±1.1 MBq (370±30 uCi), and dynamic PET study was implemented for 30 minutes according to ten 1-minute image and four 5-minute image protocols. These two stationary studies were conducted for 10, 60, 90 and 120 minutes, respectively, after the injection. Partial quantification of PET signals was executed by AMIDE software. Images were practically gained by false-color-scale in proportional to the tissue concentration (% ID/g) of a positron labeling probe. Red represents the highest concentration, while yellow, green and blue correspond to gradually lower concentrations.

PET images are shown in FIGS. 7A to 13.

Result

Verification of HER2 Expression and Affinity of Aptamer to Target Tumor Cell

Western blot and flow cytometry were performed to investigate HER2 expression in a breast cancer cell line, BT474. Through western blot analysis, over-expression in BT474 as well as SKBR3 cell line known to over-express HER2 due to gene amplification was confirmed. Further, it was found that no signal is detected at the corresponding site in a negative control cell line, MDA-MB231 (FIG. 14).

As shown in FIGS. 15A and 15B, it is proven that HER2 antibody is very specifically bound to HER2-positive BT474 cell line using the flow cytometry. As compared to the antibody, it can be seen that ERBB2 aptamer is very weak in MDA-MB231 cell line, whereas in BT474 cell line it is strongly bound thereto. Moreover, binding of the aptamer to any cell line could not be seen in random oligonucleotides. These results suggest that ERBB2 aptamer is preferentially bound to HER2-positive cell lines, and such binding may be possible by recognizing HER2 structure on the surface of the cell line. In the same manner, it was observed that KPL4 as a breast cancer cell line is strongly bound to SK-BR-3 cell line fluorescence-labeled aptamer.

Confocal Microscope Analysis

Binding of ERBB2 aptamer to cells was further assessed by a confocal microscope (FIGS. 16A and 16B). BT474 HER2-positive breast cancer cell line was treated with the aptamer. Since ERBB2 aptamer was fluorescence-labeled, fluorescence was observed on the surface of the cell, and HER2 structure present on the cell surface was identified. Fluorescence exhibited by the aptamer was observed along a cellular membrane, while MDA-MB231 cell line as a negative control group did not indicate any fluorescent signal and thus was determined not to include HER2. Accordingly, it was observed that ERBB2 aptamer could be bound to HER2-positive breast cancer cell line, but is minimally bound to HER2-negative cells. After treatment of the breast cancer cell lines KPL4, N87 and SK-BR-3 with ERBB2 aptamers {[AP001-24] and [AP001-25]}, which form complementary base pairings along with fluorescence-labeled ODN, fluorescence observation was performed using a confocal microscope by the same procedures as conducted in the above experiments. It was found that the above both types of ERBB2 aptamers were well bound to the breast cancer cell lines, wherein [AP001-24] showed fluorescence on the cell surface along the cellular membrane, while [AP001-25] showed fluorescence even inside the cell.

In Vivo PET Imaging, In Vivo Distribution, Immuno-Histochemistry

In vivo bio-molecular images of mice having BT474 or KPL4 cancer were given over time according to animal micro-PET. Referring to FIG. 17, it was observed that intake of 18F-labeled HER2-specific ERBB2 aptamer is significantly increased in tumor tissues present in the left armpit of a mouse. In images taken for 120 minutes, the cancer was distinctly labeled by ERBB2 aptamer in horizontal images and coronal images. Physiological intake clearly appearing in the intestine and bladder may reflect these organs as two major discharge routes of radiation medicine.

In vivo distribution was verified in the mice having cancer, 1 hour after injection of $^{18}$F-labeled ERBB2 aptamer. After sacrificing the animal, radiation levels in separate tissues including the cancer were measured by a gamma counter, and then expressed in % ID/g (FIG. 18) Measured results are also shown in Table 5 below.

TABLE 5

| Organs | % ID/g (±SD) |
| --- | --- |
| Blood | 0.60 ± 0.06 |
| Heart | 0.43 ± 0.03 |
| Liver | 1.11 ± 0.11 |
| Lung | 0.47 ± 0.06 |
| Spleen | 0.44 ± 0.03 |
| Kidney | 3.19 ± 1.02 |
| Stomach | 0.62 ± 0.13 |
| Small Intestine | 2.23 ± 0.81 |
| Large Intestine | 4.62 ± 1.09 |
| Muscle | 0.52 ± 0.09 |
| Femur | 0.65 ± 0.19 |
| BT474 tumor | 0.62 ± 0.04 |

The intake of $^{18}$F-labeled ERBB2 aptamer in the cancer was 0.62±0.04 per hour. Study on in vivo distribution demonstrated that the kidney and the intestine are two major discharge routes of $^{18}$F-labeled ERBB2 aptamer.

FIGS. 19A to 19C illustrate images of $^{18}$F-labeled ERBb2 aptamer in mice having HER2-positive and negative cancers, respectively. HER2 over-expressing BT474 cancer shows higher isotopic intake than HER2-negative MSA-MB231 cancer by comparison. For the purpose of semi-quantification, total activity (nCi) among VOIs (voxels- or volumes-of-interest) was calculated. As a result of comparison of T/M (tumor/muscle) intake ratio between BT474 and MDA-MB231 cell lines, HER2 over-expressed in BT474 cancer showed higher T/M ratio and contrast image (FIGS. 19A to 19C). In immuno-histochemical aspects, it was confirmed that BT474 cancers excised from separate mouse groups showed high HER2 expression, whereas MDA-MB231 cells have lower HER2 expression (FIG. 20). It was observed that BT474 cancer cells (upper row) show higher staining for HER2 in a cellular membrane than MDA-MB231 cell line (lower row) by comparison.

According to the present invention, HER2 targeting ERBB2 aptamer was successfully PET-imaged in vivo. The present invention is the first case to execute HER2 target PET imaging using ERBB2-specific aptamer. In mice with BT474 cancer, PET images demonstrated that ERBB2 aptamer may recognize HER2 in vivo and relatively distinctively show the cancer. Based on these results, the radio-labeled ERBB2 aptamer may be applied to targeted treatment of HER2-positive breast cancer cell line or potentially applied to determination of appropriate therapeutic methods for the same.

As identified in the above embodiments, when R-[ERBB2 aptamer]-ODN-X/cODN-L-F$^{18}$ (represented by R-[ERBB2 aptamer]-X-hy(bp)-L-F$^{18}$ in the above description) is prepared by combining R-[ERBB2 aptamer]-ODN-X with cODN-L-F18, the aptamer chemically modified (i.e., protected) at 5' terminal or 3' terminal position, or both of these terminal positions, for example, from R=H (No protecting) and X=H (No protecting) to R=cholesterol or PEG (polyethyleneglycol) and X=idT (inverted deoxythymidine), LNA (locked nucleic acid), 2'-methoxy nucleotide, 2'-amino nucleotide, 2'F-nucleotide, etc., may assure better images.

Since the modification due to the above compounds may improve effects of increasing $t_{1/2}$ (half-life) blood clearance, that is, increase in vivo half-life in blood, ERBB2 aptamer having a radioisotope bound thereto is increasingly bound to a tumor thus to improve imaging efficiency [as compared to $t_{1/2}$=10 minutes when R=H and X=H, $t_{1/2}$ increases to 1 hour if R and X are protected and modified, thereby demonstrating better images].

REFERENCES

1. Tuerk C, Gold L. Systematic evolution of ligands by exponential enrichment: RNA ligands to bacteriophage T4 DNA polymerase. Science. 1990; 249: 505-10.
2. Ellington A D, Szostak J W. In vitro selection of RNA molecules that bind specific ligands. Nature. 1990; 346: 818-22.
3. Stoltenburg R, Reinemann C, Strehlitz B. SELEX—a (r)evolutionary method to generate high-affinity nucleic acid ligands. Biomolecular engineering. 2007; 24: 381-403.
4. Spiridonova V A, Kopylov A M. DNA aptamers as radically new recognition elements for biosensors. Biochemistry Biokhimiia. 2002; 67: 706-9.
5. Jayasena S D. Aptamers: an emerging class of molecules that rival antibodies in diagnostics. Clinical chemistry. 1999; 45: 1628-50.
6. Bock L C, Griffin L C, Latham J A, Vermaas E H, Toole J J. Selection of single-stranded DNA molecules that bind and inhibit human thrombin. Nature. 1992; 355 (6360): 564-6.
7. Bates P J, Laber D A, Miller D M, Thomas S D, Trent J O. Discovery and development of the G-rich oligonucleotide AS1411 as a novel treatment for cancer. Experimental and molecular pathology. 2009; 86: 151-64.
8. Lupold S E, Hicke B J, Lin Y, Coffey D S. Identification and characterization of nuclease-stabilized RNA molecules that bind human prostate cancer cells via the prostate-specific membrane antigen. Cancer research. 2002; 62: 4029-33.
9. Daniels D A, Chen H, Hicke B J, Swiderek K M, Gold L. A tenaascin-C aptamer identified by tumor cell SELEX: systematic evolution of ligands by exponential enrichment. Proceedings of the National Academy of Sciences of the United States of America. 2003; 100: 15416-21.
10. James W. Aptamers in the virologists' toolkit. The Journal of general virology. 2007; 88 (Pt 2): 351-64.
11. Doggrell S A. Pegaptanib: the first antiangiogenic agent approved for neovascular macular degeneration. Expert opinion on pharmacotherapy. 2005; 6: 1421-3.
12. Dausse E, Da Rocha Gomes S, Toulme J J. aptamers: a new class of oligonucleotides in the drug discovery pipeline? Current opinion in pharmacology. 2009; 9: 602-7.
13. Mitri Z, Constantine T, O'Regan R. The HER2 Receptor in Breast Cancer: Pathophysiology, Clinical Use, and New Advances in Therapy. Chemotherapy research and practice. 2012; 2012: 743193.
14. Burstein H J. The distinctive nature of HER2-positive breast cancers. The New England journal of medicine. 2005; 353: 1652-4.
15. Tan M, Yu D. Molecular mechanisms of erbB2-mediated breast cancer chemoresistance. Advances in experimental medicine and biology. 2007; 608: 119-29.
16. Baselga J, Swain S M. Novel anticancer targets: revisiting ERBB2 and discovering ERBB3. Nature reviews Cancer. 2009; 9: 463-75.
17. Dastjerdi K, Tabar G H, Dehghani H, Haghparast A. Generation of an enriched pool of DNA aptamers for an HER2-overexpressing cell line selected by Cell SELEX. Biotechnology and applied biochemistry. 2011; 58: 226-30.
18. Liu Z, Duan J H, Song Y M, Ma J, Wang F D, Lu X et al. Novel HER2 aptamer selectively delivers cytotoxic drug to HER2-positive breast cancer cells in vitro. Journal of translational medicine. 2012; 10: 148.
19. Mahlknecht G, Maron R, Mancini M, Schechter B, Sela M, Yarden Y. Aptamer to ErbB-2/HER2 enhances degradation of the target and inhibits tumorigenic growth. Proceedings of the National Academy of Sciences of the United States of America. 2013; 110: 8170-5.
20. Mahlknecht G, Sela M, Yarden Y. Aptamer Targeting the ERBB2 Receptor Tyrosine Kinase for Applications in Tumor Therapy. Methods in molecular biology (Clifton, N.J.). 2015; 1317: 3-15.
21. Moosavian S A, Jaafari M R, Taghdisi S M, Mosaffa F, Badiee A, Abnous K. Development of RNA aptamers as molecular probes for HER2 (+) breast cancer study using cell-SELEX. Iranian journal of basic medical sciences. 2015; 18: 576-86.
22. James M L, Gambhir S S. A molecular imaging primer: modalities, imaging agents, and applications. Physiological reviews. 2012; 92: 897-965.
23. Hicke B J, Stephens A W, Gould T, Chang Y F, Lynott C K, Heil J et al. Tumor targeting by an aptamer. Journal of nuclear medicine: official publication, Society of Nuclear Medicine. 2006; 47: 668-78.
24. Jacobson O, Yan X, Niu G, Weiss I D, Ma Y, Szajek L P et al. PET imaging of tenascin-C with a radiolabeled single-stranded DNA aptamer. Journal of nuclear medicine: official publication, Society of Nuclear Medicine. 2015; 56: 616-21.
25. Pala K, Serwotka A, Jelen F, Jakimowicz P, Otlewski J. Tumor-specific hyperthermia with aptamer-tagged superparamagnetic nanoparticles. International journal of nanomedicine. 2014; 9: 67-76. and Lee J H, Chae Y C, Kim Y, Kang H, Im J H, Kim J I, Kim K S, Jang S K, Oh I U, Choi M J, Kang W J. "Aptamer which selectively binds to ERBB2 receptor and uses thereof" U S 2015/0005368 A1 (Jan. 1, 2015).
26. Flagothier J, Kaisin G, Mercier F, Thonon D, Teller N, Wouters J et al. Synthesis of two new alkyne-bearing linkers used for the preparation of siRNA for labeling by click chemistry with fluorine-18. Applied radiation and isotopes: including data, instrumentation and methods for use in agriculture, industry and medicine. 2012; 70: 1549-57.
27. Ramenda T, Steinbach J, Wuest F. 4-[18F] Fluoro-N-methyl-N-(propyl-2-yn-1-yl) benzenesulfonamide ([18F] F-SA): a versatile building block for labeling of peptides, proteins and oligonucleotides with fluorine-18 via Cu (I)-mediated click chemistry. Amino acids. 2013; 44: 1167-80.

28. Zuker M. Mfold web server for nucleic acid folding and hybridization prediction. Nucleic acids research. 2003; 31 (13): 3406-15.
29. Kibbe W A. OligoCalc: an online oligonucleotide properties calculator. Nucleic acids research. 2007; 35 (Web Server issue): W43-6.
30. Tang G, Zeng W, Yu M, Kabalka G. Facile synthesis of N-succinimidyl 4-[18F] fluorobenzoate ([18F]SFB) for protein labeling. Journal of Labelled Compounds and Radiopharmaceuticals. 2008; 51: 68-71.
31. Tang G, Tang X, Wang X. A facile automated synthesis of N-succinimidyl 4-[18F] fluorobenzoate ([18F]SFB) for 18F-labeled cell-penetrating peptide as PET tracer. Journal of Labelled Compounds and Radiopharmaceuticals. 2010; 53: 543-7.
32. Scott P J H, Shao X. Fully automated, high yielding production of N-succinimidyl 4-[18F]fluorobenzoate ([18F] SFB), and its use in microwave-enhanced radiochemical coupling reactions. Journal of Labelled Compounds and Radiopharmaceuticals. 2010; 53: 586-91.
33. Kraus M H, Popescu N C, Amsbaugh S C, King C R. Overexpression of the EGF receptor-related proto-oncogene erbB-2 in human mammary tumor cell lines by different molecular mechanisms. The EMBO journal. 1987; 6: 605-10.
34. Varmira K, Hosseinimehr S J, Noaparast Z, Abedi S M. An improved radiolabelled RNA aptamer molecule for HER2 imaging in cancers. Journal of drug targeting. 2014; 22: 116-22.
35. Bouchard P R, Hutabarat R M, Thompson K M. Discovery and development of therapeutic aptamers. Annual review of pharmacology and toxicology. 2010; 50: 237-57.
36. Sun H, Zhu X, Lu P Y, Rosato R R, Tan W, Zu Y. Oligonucleotide aptamers: new tools for targeted cancer therapy. Molecular therapy Nucleic acids. 2014; 3: e182.
37. Lao Y H, Phua K K, Leong K W. aptamer nanomedicine for cancer therapeutics: barriers and potential for translation. ACS nano. 2015; 9: 2235-54.
38. Sun H, Zu Y. A Highlight of Recent Advances in Aptamer Technology and Its Application. Molecules. 2015; 20: 11959-80.
39. Rosenberg J E, Bambury R M, Van Allen E M, Drabkin H A, Lara P N, Jr., Harzstark A L et al. A phase II trial of AS1411 (a novel nucleolin-targeted DNA aptamer) in metastatic renal cell carcinoma. Investigational new drugs. 2014; 32: 178-87.
40. Dassie J P, L I Hernandez, Thomas G S, Long M E, Rockey W M, C A Howell et al. Targeted inhibition of prostate cancer metastases with an RNA aptamer to prostate-specific membrane antigen. Molecular therapy: the journal of the American Society of Gene Therapy. 2014; 22: 1910-22.
41. Xu W, Siddiqui I A, Nihal M, Pilla S, Rosenthal K, Mukhtar H et al. Aptamer-conjugated and doxorubicin-loaded unimolecular micelles for targeted therapy of prostate cancer. Biomaterials. 2013; 34: 5244-53.
42. Lim E K, Kim B, Choi Y, Ro Y, Cho E J, Lee J H et al. Aptamer-conjugated magnetic nanoparticles enable efficient targeted detection of integrin alphavbeta3 via magnetic resonance imaging. Journal of biomedical materials research Part A. 2014; 102: 49-59.
43. Hu H, Dai A, Sun J, Li X, Gao F, Wu L et al. Aptamer-conjugated Mn3O4@SiO2 core-shell nanoprobes for targeted magnetic resonance imaging. Nanoscale. 2013; 5: 10447-54.

A sequence listing electronically submitted with the present application on Oct. 25, 2019 (filing date) as an ASCII text file named 20191025_Q16819LC39_TU_SEQ, created on Oct. 24, 2019 (saved date) and having a size of 13312 bytes, is incorporated herein by reference in its entirety.

The invention claimed is:

1. A composition for imaging a tumorous disease region, which includes HER2-specific ERBB2 aptamer, the composition comprising:
a labeled hybridized aptamer comprising an aptamer represented as formula 1 hybridized with a labeled-ODN represented as formula 2:

R-[ERBB2 aptamer]-ODN-X     [Formula 1]

where R is H, cholesterol or polyethylene glycol (PEG);
ERBB2 aptamer has SEQ ID NO: 1 or SEQ ID NO: 7;
ODN is oligodeoxynucleotide of SEQ ID NO: 36; and
X is H, idT (inverted deoxythymidine), LNA (locked nucleic acid), 2'-methoxy nucleotide, 2'-amino nucleotide, or 2'F-nucleotide;

cODN-Y     [Formula 2]

where cODN is complementary oligodeoxynucleotide of the ODN; and

Y is fluorescent dye or linker-radioisotope.

2. The composition according to claim 1, wherein the radioisotope is selected from $^{18}F$, $^{32}P$, $^{123}I$, $^{89}Zr$, $^{67}Ga$, $^{201}Tl$ and $^{111}In$-111.

3. The composition according to claim 2, wherein the radioisotope is $^{18}F$.

4. The composition according to claim 1, wherein the fluorescent dye is a cyanine fluorescent dye.

5. The composition according to claim 4, wherein the fluorescent dye is Cy5.

6. A method for providing cancer or cancer metastasis diagnostic information, comprising:
   reacting a biological sample isolated from a patient with the labeled aptamer according to claim 1;
   measuring a binding degree of the aptamer in the biological sample of the patient; and
   comparing the binding degree of the aptamer in the biological sample of the patient with the binding degree of the aptamer in a normal sample thereof.

7. The method of claim 6, wherein the aptamer includes the DNA sequence of SEQ ID NO: 36 or SEQ ID NO: 37.

8. The method of claim 6, wherein the radioisotope is selected from $^{18}F$, $^{32}P$, $^{123}I$, $^{89}Zr$, $^{67}Ga$, $^{201}Tl$ and $^{111}In$-111.

9. The method of claim 6, wherein the radioisotope is $^{18}F$.

10. The method of claim 6, wherein the fluorescent dye is a cyanine fluorescent dye.

11. The method of claim 6, wherein the fluorescent dye is Cy5.

12. A method for preparing a composition for imaging a tumorous disease region, comprising:
    reacting a cODN with Y of Formula 2 to prepare a labeled cODN represented as formula 2, and obtaining the labeled cODN; and
    preparing a labeled hybridized aptamer by hybridizing an aptamer represented as formula 1 with the labeled cODN represented as formula 2:

R-[ERBB2 aptamer]-ODN-X      [Formula 1]

where R is H, cholesterol or polyethylene glycol (PEG);
    ODN is oligodeoxynucleotide; and
    X is H, idT (inverted deoxythymidine), LNA (locked nucleic acid), 2'-methoxy nucleotide, 2'-amino nucleotide, or 2'F-nucleotide;

cODN-Y      [Formula 2]

where cODN is complementary oligodeoxynucleotide of ODN; and
    Y is fluorescent dye or linker-radioisotope.

* * * * *

SEQUENCE LISTING

```
<160> NUMBER OF SEQ ID NOS: 37

<210> SEQ ID NO 1
<211> LENGTH: 40
<212> TYPE: DNA
<213> ORGANISM: Artificial Sequence
<220> FEATURE:
<223> OTHER INFORMATION: core sequence represented by Clone No.
      9-ER-N-A01_A05
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 1
angnnagagn nngccngagn gccncgnaag ggcgnaacaa                              40

<210> SEQ ID NO 2
<211> LENGTH: 40
<212> TYPE: DNA
<213> ORGANISM: Artificial Sequence
<220> FEATURE:
<223> OTHER INFORMATION: core sequence represented by Clone No.
      9-ER-N-A02_B05
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]
```

```
<400> SEQUENCE: 2 nacnggggccc gnnagccncn ggcgcnccnn cgcnngngcc                              40

<210> SEQ ID NO 3
<211> LENGTH: 36
<212> TYPE: DNA
<213> ORGANISM: Artificial Sequence
<220> FEATURE:
<223> OTHER INFORMATION: core sequence represented by Clone No.
      9-ER-N-A03_C05
<220> FEATURE:
<221> NAME/KEY: misc_feature
<222> LOCATION: (1)..(36)
<223> OTHER INFORMATION: n is NapdU [5-(N-Naphthylcarboxyamide)-2'-
      deoxyuridine]

<400> SEQUENCE: 3
nnancaacgc acngagggcg ncagcnncnn nnnagg                                   36

<210> SEQ ID NO 4
<211> LENGTH: 39
<212> TYPE: DNA
<213> ORGANISM: Artificial Sequence
<220> FEATURE:
<223> OTHER INFORMATION: core sequence represented by Clone No.
      9-ER-N-A04_D05
<220> FEATURE:
<221> NAME/KEY: misc_feature
<222> LOCATION: (1)..(39)
<223> OTHER INFORMATION: n is NapdU [5-(N-Naphthylcarboxyamide)-2'-
      deoxyuridine]

<400> SEQUENCE: 4
angnagagnn ngccngagng ccncgcaagg gcgnaacag                                39

<210> SEQ ID NO 5
<211> LENGTH: 40
<212> TYPE: DNA
<213> ORGANISM: Artificial Sequence
<220> FEATURE:
<223> OTHER INFORMATION: core sequence represented by Clone No.
      9-ER-N-A06_E05
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 5
nccngncccg gnnacacaa gnnaaggcag ccgcnggana                                40

<210> SEQ ID NO 6
<211> LENGTH: 40
<212> TYPE: DNA
<213> ORGANISM: Artificial Sequence
<220> FEATURE:
<223> OTHER INFORMATION: core sequence represented by Clone No.
      9-ER-N-B02_F05
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 6
gncngaacac cgagannagc ngaacgaacg gnanggacgn                               40

<210> SEQ ID NO 7
<211> LENGTH: 40
```

```
<212> TYPE: DNA
<213> ORGANISM: Artificial Sequence
<220> FEATURE:
<223> OTHER INFORMATION: core sequence represented by Clone No.
      9-ER-N-B03_G05
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 7
nccnggcang nncganggag gccnnngann acagcccaga                              40

<210> SEQ ID NO 8
<211> LENGTH: 40
<212> TYPE: DNA
<213> ORGANISM: Artificial Sequence
<220> FEATURE:
<223> OTHER INFORMATION: core sequence represented by Clone No.
      9-ER-N-B04_H05
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 8
cgcgannaga ngaacgcaca anacccgnnc ngagnaaagn                              40

<210> SEQ ID NO 9
<211> LENGTH: 40
<212> TYPE: DNA
<213> ORGANISM: Artificial Sequence
<220> FEATURE:
<223> OTHER INFORMATION: core sequence represented by Clone No.
      9-ER-N-B08_A06
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 9
gncngaacac cgagannagc cgaacgaacg gnanggacgn                              40

<210> SEQ ID NO 10
<211> LENGTH: 40
<212> TYPE: DNA
<213> ORGANISM: Artificial Sequence
<220> FEATURE:
<223> OTHER INFORMATION: core sequence represented by Clone No.
      9-ER-N-B09_B06
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 10
gnnagacnga acgcacngag ggccgcagcc nancngaagg                              40

<210> SEQ ID NO 11
<211> LENGTH: 40
<212> TYPE: DNA
<213> ORGANISM: Artificial Sequence
<220> FEATURE:
<223> OTHER INFORMATION: core sequence represented by Clone No.
      9-ER-N-B12_C06
<220> FEATURE:
<221> NAME/KEY: misc_feature
```

```
<222> LOCATION: (1)..(40)
<223> OTHER INFORMATION: n is NapdU [5-(N-Naphthylcarboxyamide)-2'-
      deoxyuridine]

<400> SEQUENCE: 11
angnnagagn nngccngagn gccncgcaag ggcgnaacaa                          40

<210> SEQ ID NO 12
<211> LENGTH: 41
<212> TYPE: DNA
<213> ORGANISM: Artificial Sequence
<220> FEATURE:
<223> OTHER INFORMATION: core sequence represented by Clone No.
      9-ER-N-C03_E06
<220> FEATURE:
<221> NAME/KEY: misc_feature
<222> LOCATION: (1)..(41)
<223> OTHER INFORMATION: n is NapdU [5-(N-Naphthylcarboxyamide)-2'-
      deoxyuridine]

<400> SEQUENCE: 12
gncngagcan cgcgnnnagc cgaacgcncg gngaggnaga n                        41

<210> SEQ ID NO 13
<211> LENGTH: 40
<212> TYPE: DNA
<213> ORGANISM: Artificial Sequence
<220> FEATURE:
<223> OTHER INFORMATION: core sequence represented by Clone No.
      9-ER-N-C05_F06
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 13
ncanggcang nncganggag gccnnngann acagcccaga                          40

<210> SEQ ID NO 14
<211> LENGTH: 40
<212> TYPE: DNA
<213> ORGANISM: Artificial Sequence
<220> FEATURE:
<223> OTHER INFORMATION: core sequence represented by Clone No.
      9-ER-N-C06_G06
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 14
cnacacgaan caacnccccn ccgcanacng aacancacaa                          40

<210> SEQ ID NO 15
<211> LENGTH: 39
<212> TYPE: DNA
<213> ORGANISM: Artificial Sequence
<220> FEATURE:
<223> OTHER INFORMATION: core sequence represented by Clone No.
      9-ER-N-C08_H06
<220> FEATURE:
<221> NAME/KEY: misc_feature
<222> LOCATION: (1)..(39)
<223> OTHER INFORMATION: n is NapdU [5-(N-Naphthylcarboxyamide)-2'-
      deoxyuridine]

<400> SEQUENCE: 15
nnagcaaaan gccangngcg nccngncccg gnnnacagc                           39
```

```
<210> SEQ ID NO 16
<211> LENGTH: 40
<212> TYPE: DNA
<213> ORGANISM: Artificial Sequence
<220> FEATURE:
<223> OTHER INFORMATION: core sequence represented by Clone No.
      9-ER-N-C10_A07
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 16
ngangncccc aacncagcng ngaancnang cccccgccca                              40

<210> SEQ ID NO 17
<211> LENGTH: 40
<212> TYPE: DNA
<213> ORGANISM: Artificial Sequence
<220> FEATURE:
<223> OTHER INFORMATION: core sequence represented by Clone No.
      9-ER-N-D01_B07
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 17
cngagcggnn acnacaccac cgngagaccn nagnnacaaa                              40

<210> SEQ ID NO 18
<211> LENGTH: 40
<212> TYPE: DNA
<213> ORGANISM: Artificial Sequence
<220> FEATURE:
<223> OTHER INFORMATION: core sequence represented by Clone No.
      9-ER-N-D02_C07
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 18
annagangaa agcgcanncc aacaacagan aancngaggg                              40

<210> SEQ ID NO 19
<211> LENGTH: 40
<212> TYPE: DNA
<213> ORGANISM: Artificial Sequence
<220> FEATURE:
<223> OTHER INFORMATION: core sequence represented by Clone No.
      9-ER-N-D04_E07
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 19
nnnggagngn cnnacggnng gagnaancga ggangganga                              40

<210> SEQ ID NO 20
<211> LENGTH: 40
<212> TYPE: DNA
<213> ORGANISM: Artificial Sequence
<220> FEATURE:
```

<223> OTHER INFORMATION: core sequence represented by Clone No.
      9-ER-N-D05_F07
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 20
ccgnnaccna ccnccncgac cgngggngcc cnnagnccca                                40

<210> SEQ ID NO 21
<211> LENGTH: 39
<212> TYPE: DNA
<213> ORGANISM: Artificial Sequence
<220> FEATURE:
<223> OTHER INFORMATION: core sequence represented by Clone No.
      9-ER-N-D06_G07
<220> FEATURE:
<221> NAME/KEY: misc_feature
<222> LOCATION: (1)..(39)
<223> OTHER INFORMATION: n is NapdU [5-(N-Naphthylcarboxyamide)-2'-
      deoxyuridine

<400> SEQUENCE: 21
nccnggcang nncganggag gccnnngann acagccaga                                 39

<210> SEQ ID NO 22
<211> LENGTH: 40
<212> TYPE: DNA
<213> ORGANISM: Artificial Sequence
<220> FEATURE:
<223> OTHER INFORMATION: core sequence represented by Clone No.
      9-ER-N-D07_H07
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 22
ccgnnaccna ccnccncgac cgngggngcc nnnagnccca                                40

<210> SEQ ID NO 23
<211> LENGTH: 40
<212> TYPE: DNA
<213> ORGANISM: Artificial Sequence
<220> FEATURE:
<223> OTHER INFORMATION: core sequence represented by Clone No.
      9-ER-N-D09_A08
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 23
angnnagagn nngccngagn gccncgcaag ggcgnaacaa                                40

<210> SEQ ID NO 24
<211> LENGTH: 40
<212> TYPE: DNA
<213> ORGANISM: Artificial Sequence
<220> FEATURE:
<223> OTHER INFORMATION: core sequence represented by Clone No.
      9-ER-N-D11_B08
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

```
<400> SEQUENCE: 24
nccnggcang nncganggag gccnnngann acagcccagn                    40

<210> SEQ ID NO 25
<211> LENGTH: 40
<212> TYPE: DNA
<213> ORGANISM: Artificial Sequence
<220> FEATURE:
<223> OTHER INFORMATION: core sequence represented by Clone No.
      9-ER-N-E04_D08
<220> FEATURE:
<221> NAME/KEY: misc_feature
<222> LOCATION: (1)..(40)
<223> OTHER INFORMATION: n is NapdU [5-(N-Naphthylcarboxamide)-2'-
      deoxyuridine]

<400> SEQUENCE: 25
annagangaa agcacanncc aacaacagan aancngaggg                    40

<210> SEQ ID NO 26
<211> LENGTH: 40
<212> TYPE: DNA
<213> ORGANISM: Artificial Sequence
<220> FEATURE:
<223> OTHER INFORMATION: core sequence represented by Clone No.
      9-ER-N-E11_F08
<220> FEATURE:
<221> NAME/KEY: misc_feature
<222> LOCATION: (1)..(40)
<223> OTHER INFORMATION: n is NapdU [5-(N-Naphthylcarboxamide)-2'-
      deoxyuridine]

<400> SEQUENCE: 26
angnnagagn nngccngagn gcgncgcaag ggcgnaacag                    40

<210> SEQ ID NO 27
<211> LENGTH: 39
<212> TYPE: DNA
<213> ORGANISM: Artificial Sequence
<220> FEATURE:
<223> OTHER INFORMATION: core sequence represented by Clone No.
      9-ER-N-F05_D09
<220> FEATURE:
<221> NAME/KEY: misc_feature
<222> LOCATION: (1)..(39)
<223> OTHER INFORMATION: n is NapdU [5-(N-Naphthylcarboxamide)-2'-
      deoxyuridine]

<400> SEQUENCE: 27
ngagaagggc ngngccnnac ncaaaannng ggancngaa                     39

<210> SEQ ID NO 28
<211> LENGTH: 40
<212> TYPE: DNA
<213> ORGANISM: Artificial Sequence
<220> FEATURE:
<223> OTHER INFORMATION: core sequence represented by Clone No.
      9-ER-N-F05_D09
<220> FEATURE:
<221> NAME/KEY: misc_feature
<222> LOCATION: (1)..(40)
<223> OTHER INFORMATION: n is NapdU [5-(N-Naphthylcarboxamide)-2'-
      deoxyuridine]

<400> SEQUENCE: 28
nccnggnang nncganggag gccnnngann acagcccaga                    40

<210> SEQ ID NO 29
```

```
<211> LENGTH: 40
<212> TYPE: DNA
<213> ORGANISM: Artificial Sequence
<220> FEATURE:
<223> OTHER INFORMATION: core sequence represented by Clone No.
      9-ER-N-F08_E09
<220> FEATURE:
<221> NAME/KEY: misc_feature
<222> LOCATION: (1)..(40)
<223> OTHER INFORMATION: n is NapdU [5-(N-Naphthylcarboxamide)-2'-
      deoxyuridine]

<400> SEQUENCE: 29
nagancncng annaggnaga acgcccnacn cnaacggcag                              40

<210> SEQ ID NO 30
<211> LENGTH: 40
<212> TYPE: DNA
<213> ORGANISM: Artificial Sequence
<220> FEATURE:
<223> OTHER INFORMATION: core sequence represented by Clone No.
      9-ER-N-F09_F09
<220> FEATURE:
<221> NAME/KEY: misc_feature
<222> LOCATION: (1)..(40)
<223> OTHER INFORMATION: n is NapdU [5-(N-Naphthylcarboxamide)-2'-
      deoxyuridine]

<400> SEQUENCE: 30
ngagaagggc ngngccnnac ncaaaannng gggancngaa                              40

<210> SEQ ID NO 31
<211> LENGTH: 40
<212> TYPE: DNA
<213> ORGANISM: Artificial Sequence
<220> FEATURE:
<223> OTHER INFORMATION: core sequence represented by Clone No.
      9-ER-N-F11_G09
<220> FEATURE:
<221> NAME/KEY: misc_feature
<222> LOCATION: (1)..(40)
<223> OTHER INFORMATION: n is NapdU [5-(N-Naphthylcarboxamide)-2'-
      deoxyuridine]

<400> SEQUENCE: 31
ngagaagggc ngngccnnac ncaaaannng gggancngaa                              40

<210> SEQ ID NO 32
<211> LENGTH: 40
<212> TYPE: DNA
<213> ORGANISM: Artificial Sequence
<220> FEATURE:
<223> OTHER INFORMATION: core sequence represented by Clone No.
      9-ER-N-G04_B10
<220> FEATURE:
<221> NAME/KEY: misc_feature
<222> LOCATION: (1)..(40)
<223> OTHER INFORMATION: n is NapdU [5-(N-Naphthylcarboxamide)-2'-
      deoxyuridine]

<400> SEQUENCE: 32
cgnccnnggn gagnnngggn cngagcagga gcacgngagn                              40

<210> SEQ ID NO 33
<211> LENGTH: 40
<212> TYPE: DNA
<213> ORGANISM: Artificial Sequence
<220> FEATURE:
<223> OTHER INFORMATION: core sequence represented by Clone No.
      9-ER-N-H01_E10
<220> FEATURE:
```

```
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 33
annagangaa agcacanncc aacaacagan aancngaggg                              40

<210> SEQ ID NO 34
<211> LENGTH: 40
<212> TYPE: DNA
<213> ORGANISM: Artificial Sequence
<220> FEATURE:
<223> OTHER INFORMATION: core sequence represented by Clone No.
      9-ER-N-H03_G10
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine]

<400> SEQUENCE: 34
annagangaa agcacanncc aacaacagan aancngaggg                              40

<210> SEQ ID NO 35
<211> LENGTH: 40
<212> TYPE: DNA
<213> ORGANISM: Artificial Sequence
<220> FEATURE:
<223> OTHER INFORMATION: core sequence represented by Clone No.
      9-ER-N-H09_B11
<220> FEATURE:
<221> NAME/KEY: misc_feature
<222> LOCATION: (1)..(40)
<223> OTHER INFORMATION: n is NapdU [5-(N-Naphthylcarboxyamide)-2'-
      deoxyuridine

<400> SEQUENCE: 35
angnnagagn cngccngagn gccncgcaag ggcgnaacag                              40

<210> SEQ ID NO 36
<211> LENGTH: 15
<212> TYPE: DNA
<213> ORGANISM: Artificial Sequence
<220> FEATURE:
<223> OTHER INFORMATION: ODN

<400> SEQUENCE: 36
cagccacacc accag                                                        15

<210> SEQ ID NO 37
<211> LENGTH: 15
<212> TYPE: DNA
<213> ORGANISM: Artificial Sequence
<220> FEATURE:
<223> OTHER INFORMATION: cODN-Cy5

<400> SEQUENCE: 37
ctggtggtgt ggctg                                                        15
```